United States Patent
Ina et al.

(10) Patent No.: US 6,235,736 B1
(45) Date of Patent: May 22, 2001

(54) 3-ANILINO-2-CYCLOALKENONE DERIVATIVES

(75) Inventors: Shinji Ina; Kenjirou Yamana; Kyoji Noda; Akane Takahama; Toshihiko Akiyama, all of Omiya (JP)

(73) Assignee: Nikken Chemicals Co., Ltd., Tokyo (JP)

( * ) Notice: Subject to any disclaimer, the term of this patent is extended or adjusted under 35 U.S.C. 154(b) by 0 days.

(21) Appl. No.: 09/446,822

(22) PCT Filed: Dec. 25, 1997

(86) PCT No.: PCT/JP97/04857

§ 371 Date: Mar. 20, 2000

§ 102(e) Date: Mar. 20, 2000

(87) PCT Pub. No.: WO98/58901

PCT Pub. Date: Dec. 30, 1998

(30) Foreign Application Priority Data

Jun. 24, 1997 (JP) .................................................. 9-181884

(51) Int. Cl.$^7$ ................... A61K 31/136; A61K 31/5375; A61P 11/06; C07C 211/40; C07D 265/30
(52) U.S. Cl. ...................... 514/237.8; 514/349; 514/646; 514/658; 544/162; 546/297; 564/431; 564/433
(58) Field of Search .................................. 514/349, 658, 514/646, 237.8; 546/297; 564/433, 431; 544/162

(56) References Cited

U.S. PATENT DOCUMENTS

| | | | |
|---|---|---|---|
| 3,671,589 | 6/1972 | Watson et al. | 260/586 R |
| 3,969,409 | * 7/1976 | Miyano et al. | 260/570.5 |

FOREIGN PATENT DOCUMENTS

| | | |
|---|---|---|
| 49-5944 | 1/1974 | (JP) . |
| 49-85050 | 8/1974 | (JP) . |
| 50-157360 | 12/1975 | (JP) . |
| 59-25392 | 2/1984 | (JP) . |
| 61-57583 | 3/1986 | (JP) . |
| 5-51317 | 3/1993 | (JP) . |
| 5-97783 | 4/1993 | (JP) . |
| 5-117239 | 5/1993 | (JP) . |
| 6-100444 | 4/1994 | (JP) . |
| 6-100509 | 4/1994 | (JP) . |
| 6-100510 | 4/1994 | (JP) . |
| 7-101861 | 4/1995 | (JP) . |
| WO 94/10118 | 5/1994 | (WO) . |
| WO 94/12461 | 6/1994 | (WO) . |
| WO 95/03794 | 2/1995 | (WO) . |
| WO 95/08534 | 3/1995 | (WO) . |

OTHER PUBLICATIONS

Schaefer et al., "Oxidative Cyclization of 3–Anilino–Cyclohex–2–enones to Tetrahydrocarbazoles," Heterocycles, vol. 28 No. 2, pp. 979–985, 1989.*

W. Eilenberg et al., "Anodic Intramolecular Arylation of Enaminones" Tetrahedron Letters, vol. 25, No. 44, pp. 5023–5026, 1984.

P. J. Barnes, et al., Theophylline in the Management of Asthma: Time for Reappraisal? Eur. Respir. J. 1994, 7, 579–591.

C. D. Nicholson et al., "Differential Modulation of Tissue Function and Therapeutic Potential of Selective Inhibitors of Cyclic Nucleotide Phosphodiesterase Isoenzymes", TIPS, Jan. 1991; vol. 12, pp. 19–27.

T. J. Torphy et al., "Phosphodiesterase Inhibitors: new opportunities for the treatment of asthma", Thorax 1991; 46; 512–523.

D.C. Underwood et al., "Inhibition of Antigen–Induced Bronchoconstriction and Eosinophil Infiltration in the Guinea Pig by the Cyclic AMP–Specific Phosphodiesterase Inhibitor, Rolipram", The Journal of Pharmacology and Experimental Therapeutics, vol. 266, No. 1, pp. 306–313, Mar. 1993.

M. M. Teixeira et al., "Effects of Phosphodiesterase Isoenzyme Inhibitors on Cutaneous Inflammation in the Guinea–Pig", Br. J. Pharmacol., 1994, pp. 332–340.

(List continued on next page.)

Primary Examiner—Deborah C. Lambkin
Assistant Examiner—Sonya N. Wright
(74) Attorney, Agent, or Firm—Christie, Parker & Hale, LLP

(57) ABSTRACT

A 3-anilino-2-cycloalkenone derivative of the formula (I):

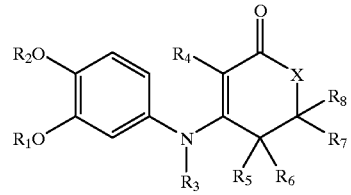

wherein, $R_1$ represents a $C_1$ to $C_8$ alkyl group, which may have a substituent, except for a methyl group, a $C_3$ to $C_7$ cycloalkyl group, a 3-tetrahydrofuryl group, an 2-indanyl group, etc., $R_2$ represents a $C_1$ to $C_4$ alkyl group, $R_3$ represents a hydrogen atom, a $C_3$ to $C_7$ alkyl group, which may have a substituent, a $C_3$ to $C_7$ cycloalkyl group, etc., $R_4$ represents a hydrogen atom, a $C_1$ to $C_5$ alkyl group, which may have a substituent, a halogen atom, etc., $R_5$, $R_6$, $R_7$, and $R_8$ independently represent a hydrogen atom, a $C_1$ to $C_5$ alkyl group, which may have a substituent, etc., X represents —$(CR_{11}R_{12})_n$—, wherein n is 0 to 2, $R_{11}$ and $R_{12}$ independently represent a hydrogen atom, a $C_1$ to $C_5$ alkyl group, which may have a substituent, etc. or —$NR_{13}$— wherein $R_{13}$ represents a hydrogen atom or a $C_1$ to $C_5$ alkyl group, which may have a substituent, and its optical isomers or their pharmaceutically acceptable salts or their hydrates or solvates.

12 Claims, No Drawings

OTHER PUBLICATIONS

N. Sommer et al., "The Antidepressant Rolipram Suppresses Cytokine Production and Prevents Autoimmune Encephalomyelits", Nature Medicine, vol. 1, No. 3, Mar. 1995, pp. 244–248.

L. Sekut et al., "Anti–inflammatory activity of phosphodiesterase (PDE)–IV Inhibitors in Acute and Chronic Models of Inflammation", Clin. Exp. Immunol. 1995; 100; pp. 126–132.

* cited by examiner

3-ANILINO-2-CYCLOALKENONE DERIVATIVES

This application is a 371 of PCT/JP97/04857 filed Dec. 25, 1997.

TECHNICAL FIELD

The present invention relates to a novel 3-anilino-2-cycloalkenone derivative having a phosphodiesterase (PDE) IV inhibitory activity.

BACKGROUND ART

The intracellular second messenger CAMP is involved in relaxation of airway smooth muscles and regulation of the functions of inflammatory cells. CAMP is broken down by phosphodiesterase (PDE) and becomes inactive 5'-AMP. It is considered that an increase in concentration of cAMP due to suppression of cAMP metabolism by PDE would give bronchodilating and anti-inflammatory actions and would exhibit a therapeutic effect on inflammatory diseases such as asthma [*Eur. Respir. J.*, 7, 579 (1994)]. Up to now, PDE has been classified into five types of isozymes (i.e., types I to V PDE). Their distributions differ among tissues [*Trends Pharmacol. Sci.*, 12, 19 (1991)]. This suggests a possibility that selective inhibitors of PDE isozymes would result in tissue specific increase of intracellular CAMP concentration.

It is reported that a specific inhibitor of type IV PDE isozyme suppresses inflammatory cells functions [*Thorax*, 46, 512 (1991)] and is useful for inflammatory diseases such as asthma [*J. Pharmacol. Exp. Ther.*, 266, 306 (1993)] and dermatitis [*Br. J. Pharmacol.*, 112, 332 (1994)] and autoimmune diseases such as multiple sclerosis [*Nature Medicine*, 1, 244 (1994)] and rheumatoid arthritis [*Clin. Exp. Immunol.*, 100, 126 (1995)]. In addition, it is thought that cardiovascular side effect caused by non-selective PDE inhibitors such as theophylline could be reduced by using selective type IV PDE inhibitor. Rolipram of the following formula (Japanese Unexamined Patent Publication (Kokai) No. 50-157360) is known as a compound having a specific inhibitory activity against type IV PDE.

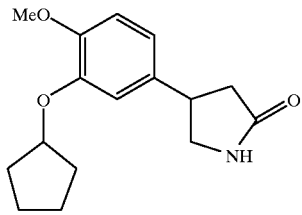

Other compounds having a specific inhibitory activity against type IV PDE are known (WO94/10118, WO94/12461, Japanese Unexamined Patent Publication (Kokai) No. 5-117239, Japanese Unexamined Patent Publication (Kokai) No. 7-101861, WO95/03794, WO95/08534, etc.), but they have not been clinically applied up to now. Development of more useful compounds is desirable.

A compound having the formula (IV):

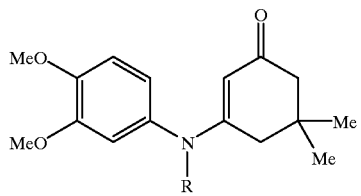

(IV)

wherein R represents a hydrogen atom or a methyl group has been known [*Tetrahedron Letter5*, 25, 5023(1984)], but there is no description regarding the physiological activity of this compound. Japanese Unexamined Patent Publication (Kokai) No. 49-85050 describes that the compound having formula (V):

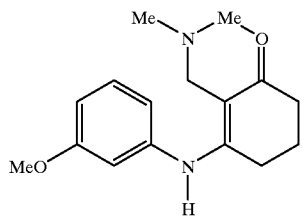

(V)

has a pharmacological action against an analgesic, sedative, antipyretic, ataractic, anticonvulsive, and other pharmacological actions against the central never system and a hypoglycemic, but does not describe a PDE IV inhibitory activity.

DISCLOSURE OF THE INVENTION

Accordingly, an object of the present invention is to provide a novel compound having a type IV PDE inhibitory activity.

In accordance with the present invention, there are provided a 3-anilino-2-cycloalkenone derivative having the formula (I):

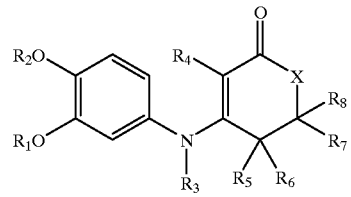

(I)

wherein $R_1$ represents a $C_1$ to $C_8$ alkyl group which may have a substituent, a $C_3$ to $C_7$ cycloalkyl group, a $C_6$ to $C_{10}$ bicycloalkyl group, a 3-tetrahydrofuryl group, or an indanyl group, $R_2$ represents a $C_1$ to $C_4$ alkyl group, $R_3$ represents a hydrogen atom, a $C_3$ to $C_7$ alkyl group which may have a substituent, a $C_3$ to $C_7$ cycloalkyl group, or an acyl group, $R_4$ represents a hydrogen atom, a $C_1$ to $C_5$ alkyl group which may have a substituent, a halogen atom, a group having the formula (II):

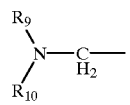

(II)

wherein $R_9$ and $R_{10}$ independently represent a $C_1$ to $C_5$ alkyl group, or a group having the formula (III):

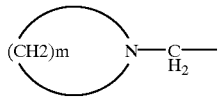
(III)

wherein, m represents an integer of 2 to 6, provided that one $CH_2$ group may be substituted with one hetero atom selected from the group consisting of oxygen, nitrogen, and sulfur, $R_5$, $R_6$, $R_7$, and $R_8$ independently represent a hydrogen atom, a $C_1$ to $C_5$ alkyl group which may have a substituent, or a phenyl group which may have a substituent, X represents —$(CR_{11}R_{12})_n$— wherein $R_{11}$ and $R_{12}$ independently represent a hydrogen atom, a $C_1$ to $C_5$ alkyl group which may have a substituent, or a phenyl group which may have a substituent, and n represents an integer of 0 to 2 provided that, when n is 0, X in the formula (I) is absent and the carbon atoms bonded to X in the formula (I) are bonded together to form a 5-membered ring, or —$NR_{13}$— wherein $R_{13}$ represents a hydrogen atom or a $C_1$ to $C_5$ alkyl group which may have a substituent, and its optical isomers or a pharmaceutically acceptable salt thereof or a hydrate thereof or a solvate thereof.

BEST MODE FOR CARRYING OUT THE INVENTION

The present inventors conducted a search for a novel is compound having a type IV PDE inhibitory activity and, as a result found that the above 3-anilino-2-cycloalkenone derivative had a strong type IV PDE inhibitory activity and had a bronchodilator and anti-inflammatory effects, whereby the present invention was completed.

The present invention will now be explained in detail below.

As the $R_1$ in the above general formula (I), a $C_1$ to $C_8$ linear or branched alkyl group (for example, methyl, ethyl, propyl, isopropyl, n-butyl, isobutyl, sec-butyl, t-butyl, n-pentyl, 1,1-dimethylpropyl, n-hexyl, 1-methylpentyl, 1,1-dimethylbutyl, n-heptyl, n-octyl) may be mentioned. These may have a substituent group (for example, a halogen atom; a hydroxyl group; a nitro group; a cyano group; an amino group; a carboxyl group; a cycloalkyl group; a haloalkyl group; a carbamoyl group; an alkoxy group; an alkylcarbonyl group; an aryl group which may include at least one hetero atom selected from the group consisting of oxygen, nitrogen, and sulfur, etc.).

As the substituted $C_1$ to $C_8$ alkyl group, for example, cyclopropylmethyl, (1-phenylcyclopropyl)methyl, (1-methylcyclopropyl)methyl, cyclobutylmethyl, cyclopentylmethyl, cyclohexylmethyl, benzyl, phenethyl, 3-phenylpropyl, 4-phenylbutyl, 1-naphthylmethyl, 2-naphthylmethyl, 2-(1-naphthyl)ethyl, 2-(2-naphthyl)ethyl, 2-indanylmethyl, 2-(2-indanyl)ethyl, etc. may be mentioned. Here, an unsubstituted methyl group is excluded from $R_1$. Further, as $R_1$, a $C_3$ to $C_7$ cycloalkyl group (for example, cyclopropyl, cyclobutyl, cyclopentyl, cyclohexyl, cycloheptyl, etc.), a $C_6$ to $C_{10}$ bicycloalkyl group [(1RS,2RS,4SR)bicyclo[2.2.1]hept-2-yl group, etc.], 3-tetrahydrofuryl, or indanyl may be mentioned. As $R_1$, preferably a $C_4$ to $C_6$ alkyl group, a $C_4$ to $C_7$ cycloalkyl group, a $C_6$ to $C_8$ bicycloalkyl group, a $C_1$ to $C_5$ alkyl group having, as a substituent group, a phenyl group, a naphthyl group, an indanyl group, or a $C_3$ to $C_7$ cycloalkyl group which may have a substituent, a 3-tetrahydrofuryl group, or an indanyl group may be mentioned. More preferably cyclopentyl, cyclohexyl, cyclopropylmethyl, cyclopentylmethyl, 2-(2-indanyl)ethyl, (1RS,2RS,4SR) bicyclo[2.2.1]hept-2-yl, or 2-indanyl may be mentioned.

As $R_2$, a $C_1$ to $C_4$ linear or branched alkyl group (for example, methyl, ethyl, n-propyl, isopropyl, n-butyl, sec-butyl, t-butyl, etc.) may be mentioned. Preferably, methyl or ethyl, more preferably methyl may be mentioned.

As $R_3$, a $C_1$ to $C_5$ linear or branched alkyl group (for example, methyl, ethyl, n-propyl, isopropyl, n-butyl, sec-butyl, t-butyl, n-pentyl, etc.) may be mentioned. These may have a substituent group (for example, a halogen atom; a hydroxyl group; a nitro group; a cyano group; an amino group; a carboxyl group; a cycloalkyl group; a haloalkyl group; a carbamoyl group; an alkoxy group; an alkylcarbonyl group; an aryl group which may include at least one hetero atom selected from the group consisting of oxygen, nitrogen, and sulfur, etc.). As the substituted $C_1$ to $C_5$ alkyl group, for example, benzyl, phenethyl, 3-phenylpropyl, 4-phenylbutyl, 5-phenylpentyl, 1-naphthylmethyl, 2-naphthylmethyl, 2-pyridylmethyl, 3-pyridylmethyl, 4-pyridylmethyl, furylmethyl, thiazolylmethyl, 2-quinolylmethyl, etc. may be mentioned. Further, as $R_3$, a hydrogen atom, a $C_3$ to $C_7$ cycloalkyl group (e.g., cyclopropyl, cyclobutyl, cyclopentyl, cyclohexyl, cycloheptyl, etc.) or an acyl group (e.g., formyl, acetyl, propionyl, benzoyl, etc.) may be mentioned. As $R_3$, preferably a hydrogen atom; a $C_1$ to $C_5$ alkyl group; a $C_3$ to $C_7$ cycloalkyl group; or a $C_1$ to $C_2$ alkyl group which may have, as a substituent group, an aryl group which may include at least one hetero atom selected from the group consisting of oxygen, nitrogen, and sulfur may be mentioned. More preferably, a hydrogen atom, methyl, propyl, pentyl, cyclopentyl, 2-pyridylmethyl, 3-pyridylmethyl, 4-pyridylmethyl, benzyl, 2-quinolylmethyl, 1-naphthylmethyl, 2-naphthylmethyl, or acetyl may be mentioned.

As $R_4$, a hydrogen atom, a $C_1$ to $C_5$ linear or branched alkyl group (e.g., methyl, ethyl, propyl, isopropyl, butyl, sec-butyl, t-butyl, pentyl, etc.) may be mentioned. These may have a substituent group (e.g., a halogen atom; a hydroxyl group; a nitro group; a cyano group; an amino group; a carboxyl group; a cycloalkyl group; a haloalkyl group; a carbamoyl group; an alkoxy group; an alkylcarbonyl group; an aryl group which may include at least one hetero atom selected from the group consisting of oxygen, nitrogen, and sulfur, etc.). Further, as the $R_4$, a halogen atom (e.g., a chlorine atom, a bromine atom, an iodine atom, etc.) or a group having the following general formula (II) or general formula (III) may be mentioned.

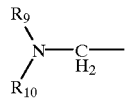
(II)

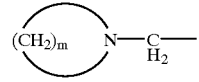
(III)

As the $R_9$ and $R_{10}$ having the above formula (II), independently, a $C_1$ to $C_5$ linear or branched alkyl group (e.g., methyl, ethyl, propyl, isopropyl, butyl, sec-butyl, t-butyl, pentyl, etc.) may be mentioned. As specific examples of the group having the above formula (II), a 1-azetidinylmethyl group, a 1-pyrrolidinylmethyl group, a 1-piperidinylmethyl group, a 1-homopiperidinylmethyl group, a 1-piperadinylmethyl group, a morpholinomethyl group, etc. may be mentioned.

The m in the general formula (III) represents an integer of 2 to 6. Further one $CH_2$ group may be substituted with at least one hetero atom selected from the group consisting of oxygen, nitrogen, and sulfur. As $R_4$, preferably a hydrogen atom, a halogen atom, a $C_1$ to $C_3$ alkyl group, a dimethylaminomethyl group, a morpholinomethyl group, or a benzyl group may be mentioned.

As $R_5$, $R_6$, $R_7$, and $R_8$, independently, a hydrogen atom, a $C_1$ to $C_5$ linear or branched alkyl group (e.g., methyl, ethyl, propyl, isopropyl, butyl, sec-butyl, t-butyl, pentyl, etc.) or a phenyl group (e.g., phenyl, 4-methylphenyl, 4-chlorophenyl, etc.) may be mentioned. The $C_1$ to $C_5$ alkyl group and phenyl group may have a substituent group (e.g., a halogen atom; a hydroxyl group; a nitro group; a cyano group; an amino group; a carboxyl group; an alkyl group; a cycloalkyl group; a haloalkyl group; a carbamoyl group; an alkoxyl group; an alkylcarbonyl group; an aryl group which may include at least one hetero atom selected from the group consisting of oxygen, nitrogen, and sulfur, etc.). As $R_5$, $R_6$, $R_7$, and $R_8$, preferably a hydrogen atom or a methyl group may be mentioned.

As X, —$(CR_{11},R_{12})_n$—, wherein, $R_{11}$, and $R_{12}$ independently represent a hydrogen atom, an unsubstituted or substituted $C_1$ to $C_5$ alkyl group, or an unsubstituted or substituted phenyl group, n represents an integer of 0 to 2 provided that, when n is 0, X in the formula (I) is absent and the carbon atoms bonded to X in the formula (I) are bonded together to form a 5-membered ring, or —$NR_{13}$—, wherein $R_{13}$ represents a hydrogen atom, a $C_1$ to $C_5$ linear or branched alkyl group (e.g., methyl, ethyl, propyl, isopropyl, butyl, sec-butyl, t-butyl, pentyl, etc.) may be mentioned. It may have a substituent group (e.g., a halogen atom; a hydroxyl group; a nitro group; a cyano group; an amino group; a carboxyl group; a cycloalkyl group; a haloalkyl group; a carbamoyl group; an alkoxyl group; an alkylcarbonyl group; an aryl group which may include at least one hetero atom selected from the group consisting of oxygen, nitrogen, and sulfur, etc.). As examples of a substituted alkyl group, benzyl, phenethyl, 3-phenylpropyl, 4-phenylbutyl, 5-phenylpentyl, pyridylmethyl, furylmethyl, or thiazolylmethyl may be mentioned. As X, preferably a case of —$(CR_{11}R_{12})_n$—, where n is 0 or 1 (when n is 1, $R_{11}$ and $R_{12}$ are preferably, independently, a hydrogen atom or a methyl group) or a case of —$NR_{13}$— where $R_{13}$ is a hydrogen atom, a $C_1$ to $C_3$ alkyl group, or a benzyl group may be mentioned.

As specific compounds having the above formula (I), the compounds produced in the Examples shown below may be mentioned.

The compound having the above general formula (I) have asymmetric carbon atoms and include optical isomers. The optical isomers are also within the scope of the present invention. Further, salts of the compounds having the above general formula (I) and their optical isomers are also included in the present invention. As the salts, pharmaceutically acceptable salts are preferred For example, inorganic acid salts such as hydrochlorides, hydrobromides, hydroiodides, and phosphates, etc. and organic acid salts such as oxalates, maleates, fumarates, lactates, malates, citrates, tartarates, benzoates, methanesulfonates, and p-toluenesulfonates, etc. may be mentioned.

Further, the present invention includes hydrates and solvates of the compounds having the above general formula (I), their optical isomers, and their salts. As the solvent for the solvates, methanol, ethanol, isopropanol, butanol, acetone, ethyl acetate, chloroform, etc. may be mentioned.

The compound having the above general formula (I) may be produced by a known method (Japanese Unexamined Patent Publication (Xokai) No. 49-85050). Examples of the production method will be explained with reference to the following reaction schemes.

Production Method 1

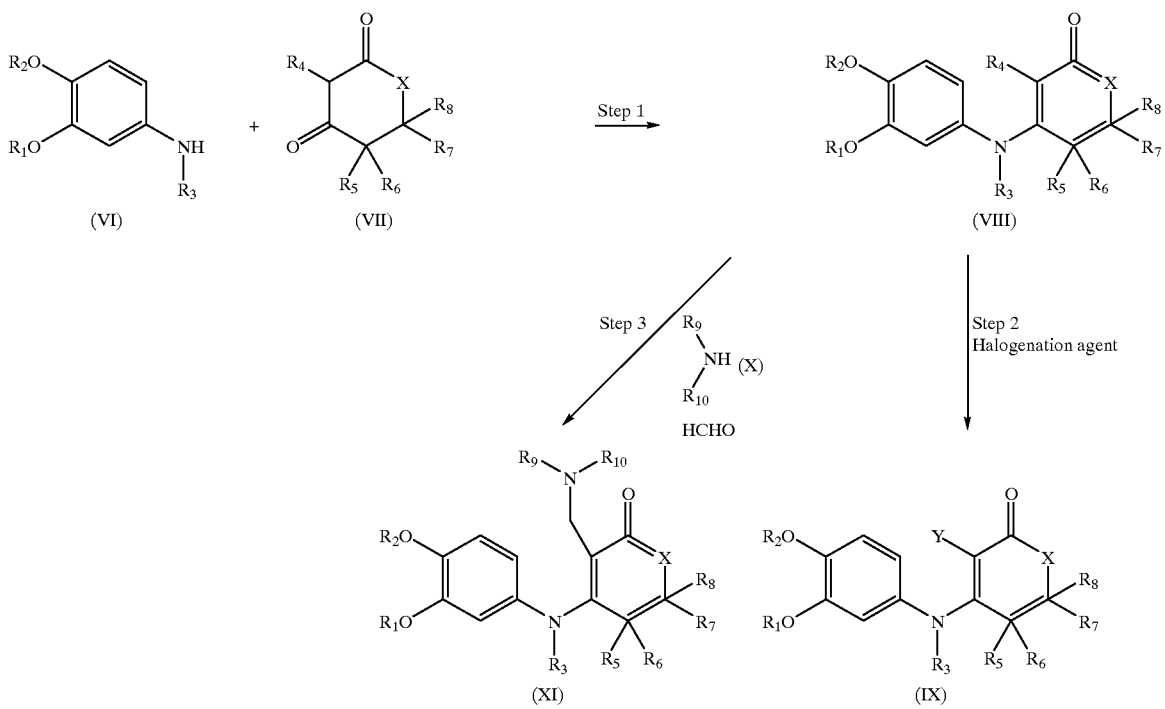

The compounds (VIII), (IX), and (XI) in the above reaction scheme each correspond to a compound having the above general formula (I).

Step 1: The compound (VIII) is synthesized from the aniline derivative(VI) and 1,3-dione (VII) by a dehydration condensation reaction. The reaction is carried out in the presence or absence of a solvent, which does not affect the reaction (e.g., an aliphatic hydrocarbon such as pentane and hexane; a halogenated hydrocarbon such as dichloromethane, chloroform, and carbon tetrachloride; an aromatic hydrocarbon such as benzene and toluene; an ether such as diethyl ether, tetrahydrofuran, and dioxane; an alcohol such as methanol and ethanol; dimethylformamide; etc.) The reaction temperature is not particularly limited, but the reaction is carried out normally from room temperature to the boiling point of the reaction solvent. Further, in some cases, a condensation agent (for example, anhydrous potassium carbonate, anhydrous sodium carbonate, p-toluenesulfonic acid, calcium chloride, or acetic acid) may be added. when an aromatic hydrocarbon (benzene, toluene, etc.) is used as the reaction solvent, the reaction may be carried out, while azeotropically separating the water produced. The compound obtained by this reaction can be purified by known methods (for example, crystallization, recrystallization, chromatography, etc.)

Step 2: A compound (VIII) where $R_4$ is a hydrogen atom is reacted with a halogenating agent to give the compound (IX), where Y is a halogen atom. As the halogenating agent, for example, N-chlorosuccinimide, N-bromosuccinimide, and N-iodosuccinimide may be used. The solvent may be any which does not affect the reaction. For example, ethanol, methanol, water, etc. is preferable. The compound obtained by this reaction is purified by known methods (for example, crystallization, recrystallization, chromatography, etc.)

Step 3: According to the production method described in Japanese Unexamined Patent Publication (Kokai) No. 49-85050, a compound (VIII), where $R_4$ is a hydrogen atom is reacted with an amino alcohol generated by an amine (X) and formaldehyde in a reaction system to give the compound (XI). The compound obtained is purified by known methods (for example, crystallization, recrystallization, chromatography, etc.)

The compounds (XIV) and (XV) in the above reaction scheme correspond to compounds having the above general Formula (I).

Step 4: According to the same method as in the above step 1, the compound (XII) is reacted with the compound (VII) give to the compound (XIII).

Step 5: The hydroxyl group of the compound (XIII) is alkylated to give the compound (XIV). As the alkylation method, the method of causing a reaction with an alkyl halide ($R_1$—Z) (wherein, Z indicate a halogen atom) in the presence of a base (e.g., potassium carbonate, sodium hydride, etc.), the method of dehydration condensation with the alcohol derivative ($R_1$—OH) by a Mitsunobu reaction, etc. may be mentioned.

Step 6: When the compound (XIV) is further reacted with an alkyl halide ($R_3$—Z), (wherein Z indicates a halogen atom) in the presence of a base such as sodium hydride, the compound (XV) is obtained.

The starting materials used in the production method 1 and the production method 2 may be commercially available compounds, but the 1,3-dione may also be produced by known methods (Japanese Unexamined Patent Publication (Rokai) No. 59-25392, Japanese Unexamined Patent Publication (Kokai) No. 61-57583, U.S. Pat. No. 3,671,589).

When the compound of the present invention is used as a therapeutic agent, it can be administered alone or together with a pharmaceutically acceptable carrier. The composition is determined by the solubility of the compound, its chemical properties, the delivery route, medication plan, etc.

For example, it may be orally administered in the form of granules, powders, tablets, pills, hard gelatin capsules, soft gelatin capsules, syrups, emulsions, suspensions, or liquids or may be administered by non-oral route such as an injection (intravenous, intramuscular, subcutaneous), ointments, suppositories, aerosols, etc. Alternatively, it may be made a powder for injection which is prepared at the time of use. Pharmaceutical use organic or inorganic solid or

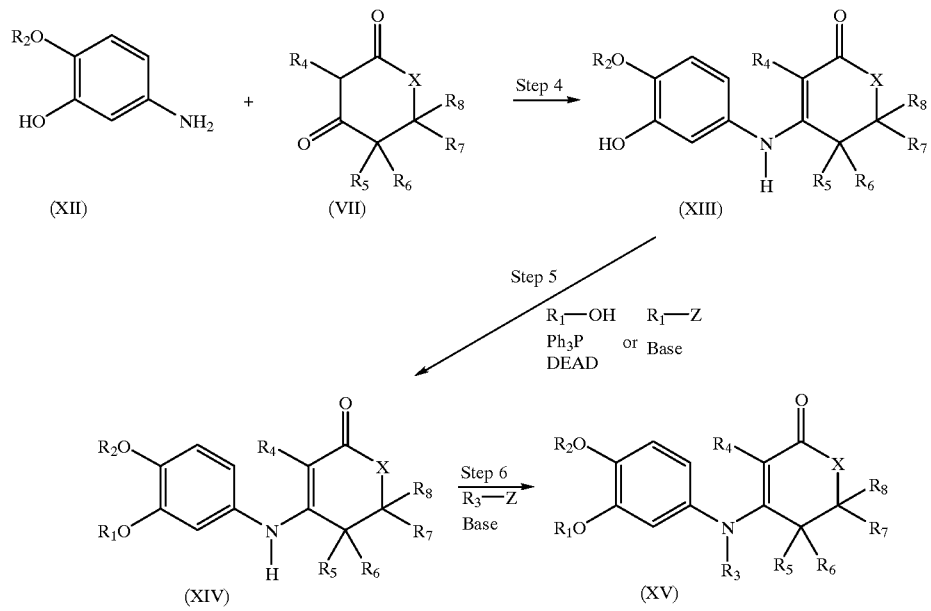

Production Method 2 liquid carriers or diluents which are suitable for oral, rectal, non-oral, and topical administration may be used together with the compound of the present invention. For example, in the case of an oral administration, the compound can be prepared in the desired form by using an excipient such as lactose, D-glucose, corn starch, or sucrose, a disintegrants such as calcium carboxymethylcellulose or hydroxypropylcellulose, a lubricants such as calcium stearate, magnesium stearate, talc, polyethylene glycol, or hydrogenated oil, a humectants such as hydroxypropylcellulose, hydroxypropylmethylcellulose, carboxymethylcellulose, polyvinyl alcohol, gelatin, or arabia gum, and a surfactant and flavoring agents, etc. may be used to prepare the desired form of administration, if necessary.

Further, in the case of a non-oral preparation, a diluent such as water, ethanol, glycerine, propylene glycol, polyethylene glycol, agar, or tragacanth gum may be used and if necessary a solution adjuvant, buffer, preservative, flavoring agent, colorant, etc. may be used. Pharmaceutical compositions may be prepared by general methods.

The clinical dosage generally ranges 0.01 to 1000 mg in terms of the compound of the present invention per adult per day when orally administered, preferably 0.01 to 100 mg, but it is more preferable to suitably adjust this depending upon the age, condition, symptoms, other drugs administered at the same time, etc. The daily dosage of the drug (i.e., the compound of the present invention) may be administered once a day or twice or three times a day with suitable intervals or intermittently. Further, when used as an injection, one dosage in an amount of 0.001 to 100 mg per adult in terms of the compound of the present invention is preferably administered continuously or intermittently. Further, when used as a topical agent, a substrate containing, for an adult, 0.01 to 1.0% of the compound of the present invention is coated one or more times at the affected location, but it is preferable to suitably adjust this in accordance with the age, disease conditions, symptoms, existence of concomitant administration, etc.

The present invention will be explained more specifically below with reference to the Examples and Test Examples, but of course the present invention is not limited in scope by these Examples and Test Examples.

EXAMPLES

Example 1

Synthesis of 3-(3-cyclopentyloxy-4-methoxyanilino)-2-cyclopenten-1-one (Compound No. 1 of Table 1)

(1) Synthesis of 3-cyclopentyloxy-4-methoxynitrobenzene 10.00 g (59 mmole) of 2-methoxy-5-nitrophenol, 11.01 g (74 mmole) of bromocyclopentane, 10.21 g (74 mmole) of potassium carbonate, and 0.98 g of potassium iodide were added in 50 ml of N,N-dimethylformamide and the mixture was stirred for one night at room temperature. This solution was diluted with 200 ml of methylene chloride and washed with water. The organic solution was dried over anhydrous magnesium sulfate, the solvent was evaporated in vacuo, to obtain a residue as a yellow solid. This residue was purified by flash chromatography ($SiO_2$: eluted by gradient of range from 40% ethyl acetate/hexane to 45% ethyl acetate/hexane). The solvent was removed and the residue dried in vacuo to obtain 3-cyclopentyloxy-4-methoxynitrobenzene 12.52 g (yield 89.3%) as a yellow solid.

$^1$H-NMR (400 MHz, $CDCl_3$) δ 1.64–1.68 (2H, m), 1.83–1.92 (4H, m), 1.99–2.05 (2H, m), 3.95 (3H, s), 4.85 (1H, m), 6.89 (1H, d, J=8.79 Hz), 7.74 (1H, d, J=2.44 Hz), 7.88 (1H, dd, J=8.79, 2.44 Hz)

(2) Synthesis of 3-cyclonentyloxy-4-methoxyaniline 1.50 g (6.32 mmole) of 3-cyclopentyloxy-4-methoxynitrobenzene was dissolved in a solution of 20 ml of methanol and 4 ml of methylene chloride. To this solution was added 150 mg of 10% Pd/C. Under $H_2$ stream (pressurized to 4.0 kgf/cm$^2$), the mixture was vigorously stirred for 1 hour. Next, the undissolved material in the reaction solution was removed by filtration and the filtrate was evaporated in vacuo to obtain a crude product 1.31 g as a brown oil. The crude product obtained here had a sufficient purity without purification, so could be used for the next reaction as it was.

$^1$H-NMR (400 MHz, $CDCl_3$) δ 1.55–1.63 (2H, m), 1.80–1.92 (6H, m), 3.41 (2H, broad s), 3.77 (3H, s), 4.72 (1H, m), 6.22 (1H, dd, J=8.30, 2.44 Hz), 6.31 (1H, d, J=2.44 Hz), 6.70 (1H, d, J=8.30 Hz)

(3) Synthesis of 3–13-cyclopentyloxy-4-methoxyanilino)-2-cyclopenten-1-one 1.04 g (5.02 mole) of 3-cyclopentyloxy-4-methoxyaniline, 0.51 g (5.02 mmole) of 1,3-cyclopentanedione, and 0.03 g of p-toluenesulfonic acid were dissolved in 30 ml of benzene and the solution was heated reflux in an apparatus fitted with a water separation tube for 3 hours, while azeotropically separating the water produced. After the reaction, the solution was cooled to room temperature, a yellow crystal was precipitated. The precipitated yellow crystal was collected by suction filtration, and the crystal was washed with diethyl ether, then dried to obtain the title compound 1.16 g (yield 80.4%) as a pale yellow crystal.

$^1$H-NMR (400 MHz, $CDCl_3$) δ 1.52–1.63 (2H, m), 1.81–1.96 (6H, m), 2.47 (2H, m), 2.73 (2H, m), 3.84 (3H, s), 4.72 (1H, m), 5.46 (1H, s), 6.41 (1H, broad s), 6.67 (1H, dd, J=8.30, 2.44 Hz), 6.73 (1H, d, J=2.44 Hz), 6.82 (1H, d, J=8.30 Hz).

Example 2

Synthesis of 3-13-cyclopentyloxy-4-methoxyanilino)-2-cyclohexen-1-one (Compound No. 2 of Table 1)

0.98 g (4.73 mmole) of the 3-cyclopentyloxy-4-methoxyaniline produced in Example 1(2) and 0.53 g (4.73 mmole) of 1,3-cyclohexanedione were dissolved in 50 ml of benzene. According to the similar procedure as Example 1(3), the title compound 1.25 g (yield 87.9%) was obtained as a yellow solid.

$^1$H-NMR (400 MHz, $CDCl_3$) δ 1.55–1.96 (8H, m), 2.03 (2H, m, J=6.35 Hz), 2.35 (2H, t, J=6.35 Hz), 2.48 (2H, t, J=6.35 Hz), 3.83 (3H, s), 4.71 (1H, m), 5.43 (1H, s), 6.17 (1H, broad s), 6.67–6.69 (2H, m), 6.80 (1H, m).

Example 3

Synthesis of 3-(3-cycloientyloxy-4-methoxyanilino)-5,5-dimethyl-2-cyclohexen-1-one (Compound No. 3 of Table 1)

0.91 g (4.40 mmole) of the 3-cyclopentyloxy-4-methoxyaniline produced in Example 1(2) and 0.62 g (4.40 mmole) of dimedone were dissolved in 30 ml of benzene and heated reflux in an apparatus similar to that of Example 1(3) for 5 hours. After the reaction, the benzene was removed in vacuo to obtain a residue as a brown oil. The residue was purified by flash chromatography ($SiO_2$: eluted by gradient in range from 2% methanol/methylene chloride to 4% methanol/methylene chloride). The solvent was removed and the residue dried in vacuo to obtain the title compound 0.98 g (yield 67.6%) as a yellow solid.

$^1$H-NMR (400 MH2, CDCl$_3$) δ 1.11 (6H, s), 1.52–1.66 (2H, m), 1.74–2.00 (6H, m), 2.21 (2H, s), 2.31 (2H, s), 3.83 (3H, s), 4.72 (1H, m), 5.43 (1H, s), 6.09 (1H, broad s), 6.68–6.70 (2H, m), 6.80 (1H, m).

Example 4

Synthesis of 3-(3-cycloientyloxy-4-methoxyanilino)-2-methyl-2-cyclopenten-1-one (Compound No. 4 of Table 1)

0.91 g (4.40 mmole) of 3-cyclopentyloxy-4-methoxyaniline produced in Example 1(2), 0.49 g (4.40 mole) of 2-methyl-1,3-cyclopentanedione, and 0.02 g of p-toluenesulfonic acid were dissolved in 50 ml of benzene. The rest of the procedure was performed based on Example 1(3), the title compound 1.27 g (yield 96.2%) was obtained as a black oil.

$^1$H-NMR (400 MHz, CDCl$_3$) δ 1.68 (3H, s), 1.61–1.96 (8H, m), 2.38–2.40 (2H, m), 2.56 (2H, m), 3.86 (3H, s), 4.75 (1H, m), 6.53 (1H, broad s), 6.69–6.72 (2H, m), 6.82–6.84 (1H, m).

Example 5

Synthesis of 3-(3-cycloientyloxy-4-methoxyanilino)-5-methyl-2-cyclohexen-1-one (Compound No. 5 of Table 1)

According to the similar procedure as in Example 1(3), using 0.83 g (4.01 mmole) of the 3-cyclopentyloxy-4-methoxyaniline produced in Example 1(2) and 0.51 g (4.01 mmole) of 5-methyl-1,3-cyclohexanedione, the title compound 1.12 g (yield 88.2%) was obtained as a light yellow solid.

$^1$H-NMR (400 MHz, CDCl$_3$) δ 1.08 (3H, d, J=5.86 Hz), 1.55–1.61 (2H, m), 1.77–1.96 (6H, m), 2.00–2.08 (1H, m), 2.22–2.31 (2H, m), 2.36–2.42 (2H, m), 3.82 (3H, s), 4.70 (1H, m), 5.41 (1H, s), 6.37 (1H, broad s), 6.66–6.68 (2H, m), 6.78–6.80 (2H, m).

Example 6

Synthesis of 2-chloro-3-(3-cyclopentyloxy-4-methoxyanilino)-2-cyclopenten-1-one (Compound No. 6 of Table 1)

To a solution 0.49 g (1.69 mmole) of the 3-(3-cyclopentyloxy-4-methoxyanilino)-2-cyclopenten-1-one produced in Example 1(3) in 5 ml of an ethanol-water (9:1) solution was added 0.25 g (1.86 mmole) of N-chlorosuccinimide. The mixture was stirred at room temperature for 1.5 hours. After the reaction, the solvent was removed in vacuo. Next, the residue obtained was diluted with 100 ml of ethyl acetate and the solution was successively washed with a saturated sodium hydrogencarbonate solution and brine. The organic solution was dried over anhydrous magnesium sulfate, then the solvent was removed in vacuo to obtain a crude product as a black oil. The crude product obtained here was purified by flash chromatography. The solvent was removed and the residue dried in vacuo to obtain the title compound 0.45 g (yield 82.5%) as a light pink solid.

$^1$H-NMR (400 MHz, CDCl$_3$) δ 1.53–1.72 (2H, m), 1.92–2.10 (6H, m), 2.48 (2H, m), 2.68 (2H, m), 3.90 (3H, s), 4.86 (1H, m), 6.74–6.75 (2H, m), 6.85 (1H, d, J=8.30 Hz), 7.25 (1H, broad s).

Example 7

Synthesis of 2-bromo-3-(3-cyclopentyloxy-4-methoxyanilino)-2-cyclopenten-1-one (Compound No. 7 of Table 1)

According to the same procedure as in Example 6, using N-bromosuccinimide, instead of the N-chlorosuccinimide, the title compound (yield 61.0%) was obtained as a gray solid.

$^1$H-NMR (400 MHz, CDCl$_3$) δ 1.55–1.72 (2H, m), 1.74–2.05 (6H, m), 2.51 (2H, m), 2.69 (2H, m), 3.86 (3H, s), 4.76 (1H, m), 6.75–6.77 (2H, m), 6.86 (1H, d, J=7.81 Hz), 7.28 (1H, broad s).

Example 8

Synthesis of 3-[3-[(1RS,2RS,4SR)-bicyclo[2.2.1]hept-2-yloxy]-4-methoxyanilino]-2-cyclopenten-1-one (Compound No. 8 of Table 1)

(1) Synthesis of 3-[(1RS,2RS,4SR)-bicyclo[2.2.1]hept-2-yloxy]-4-methoxynitrobenzene 1.50 g (8.87 mmole) of 2-methoxy-5-nitrophenol, 1.04 g (8–87 mmole) of rel(1R,2S,4S)-2-hydroxybicyclo[2.2.1]heptane, and 3.49 g (13.30 mmole) of triphenylphosphine were dissolved in 50 ml of dried tetrahydrofuran. To this solution was carefully dropwise added 2.32 g (13.30 mmole) of diethylazodicarboxylate. The reaction solution was heated reflux for 22 hours, then was diluted with 100 ml of diethyl ether and successively washed with sodium hydroxide solution (1n) and water. The organic solution was dried over anhydrous magnesium sulfate and the solvent was removed in vacuo to obtain a residue as a brown oil. The residue was purified by flash chromatography (SiO$_2$: eluted by 50% hexane/methylene chloride). The solvent was removed and the residue dried in vacuo to obtain 3-[(1RS,2RS,4SR)-bicyclo[2.2.1]hept-2-yloxy]-4-methoxynitrobenzene 2.04 g (yield 87.2%) as a yellow solid.

$^1$H-NMR (400 MHZ, CDCl$_3$) δ 1.18–1–26 (3H, m), 1.49–1.65 (3H, m), 1.73 (1H, m), 1.83–1.88 (1H, m), 2.36 (1H, m), 2.54 (1H, m), 3.94 (3H, s), 4.27 (1H, m), 6.88 (1H, d, J=8.79 Hz), 7.69 (1H, d, J=2.44 Hz), 7.87 (1H, dd, J=8.79, 2.44 Hz).

(2) Synthesis of 3-[(1RS,2RS,4SR)-bicyclo[2.2.1]hept-2-yloxy]-4-methoxyaniline

According to the same procedure as in Example 1(2), using 3-[(1RS,2RS,4SR)-bicyclo[2.2.1]hept-2-yloxy]-4-methoxynitrobenzene instead of 3-cyclopentyloxy-4-methoxynitrobenzene, 3-[(1RS,2RS,4SR)-bicyclo[2.2.1]hept-2-yloxy]-4-methoxyaniline was obtained as a purple oil.

$^1$H-NMR (400 MHz, CDCl$_3$) δ 1.08–1.19 (3H, m), 1.43–1.65 (3H, m), 1.71–1.76 (2H, m), 2.31 (1H, m), 2.50 (1H, m), 2.55–2.56 (2H, m), 3.76 (3H, s), 4.13 (1H, m), 6.21 (1H, dd, J=8.30, 2.44 Hz), 6.28 (1H, d, J=2.44 Hz), 6.70 (1H, d, J=8.30 Hz).

(3) Synthesis of 3-[3-[(1RS,2RS,4SR)-bicyclo[2.2.1]hept-2-yloxy]-4-methoxyanilino]-2-cyclopenten-1-one According to the same procedure as in Example 1(3), using 3-[(1RS,2RS,4SR)-bicyclo[2.2.1]hept-2-yloxy]-4-methoxyaniline instead of 3-cyclopentyloxy-4-methoxyaniline, the title compound (yield 85.0%) was obtained as a yellow solid.

$^1$H-NMR (400 MHz, CDCl$_3$) δ 1.12–1.22 (3H, m), 1.49–1.62 (3H, m), 1.74 (2H, m), 2.33 (1H, m), 2.46–2.50

(3H, m), 2.71–2.74 (2H, m), 3.84 (3H, s), 4.14 (1H, m), 5.45 (1H, s), 6.47 (1H, broad s), 6.66–6.68 (2H, m), 6.82 (1H, d, J=8.30 Hz).

Example 9

Synthesis of 3-[3-(2-indanyloxy)-4-methoxyanilino]-2-cyclopenten-1-one (Compound No. 9 of Table 1)

(1) Syntbesis of 3-(2-indanyloxy)-4-methoxynitrobenzene 10.00 g (59.12 mmole) of $^2$-methoxy-5-nitrophenol, 7.93 g (59.12 mmole) of 2-indanol, and 18.60 g (70.94 mmole) of triphenylphosphine were dissolved in 250 ml of dried tetrahydrofuran. To this solution was carefully dropwise added at room temperature 12.36 g (70.94 mmole) of diethylazodicarboxylate. The solution was stirred at room temperature for one night, then the solution was diluted with 250 ml of diethyl ether and successively washed with IN sodium hydroxide aqueous solution and water. The organic solution was dried over anhydrous magnesium sulfate and the solvent was removed in vacuo to obtain a residue as a light yellow solid. The residue was purified by flash chromatography (SiO$_2$: eluted by 50% hexane/methylene chloride). The solvent was removed and the residue dried in vacuo to obtain 3-(2-indanyloxy)-4-methoxynitrobenzene 12.65 g (yield 75.0%) as a light yellow solid.

$^1$H-NMR (400 MHz, CDCl$_3$) δ 3.26 (2H, dd, J=17.09, 3.42 Hz), 3.48 (2H, dd, J=17.09, 6.83 Hz), 3.91 (3H, s), 5.26 (1H, m), 6.90 (1H, d, J=8.79 Hz), 7.19–7.29 (4H, m), 7.81 (1H, d, J=2.44 Hz), 7.93 (1H, dd, J=8.79, 2.44 Hz)

(2) Synthesis of 3-(2-indanyloxy)-4-methoxyaniline

According to the same procedure as in Example 1(2), using 3-(2-indanyloxy)-4-methoxynitrobenzene, instead of 3-cyclopentyloxy-4-methoxynitrobenzene, 3-(2-indanyloxy)-4-methoxyaniline was obtained as a purple oil.

$^1$H-NMR (400 MHz, CDCl$_3$) δ 3.23 (2H, dd, J=16.60, 3.90 Hz), 3.35 (2H, dd, J=16.60, 6.35 Hz), 3.72 (3H, s), 5.15 (1H, m), 6.27 (1H, dd, J=8.30, 2.44 Hz), 6.37 (1H, d, J=2.44 Hz), 6.73 (1H, d, J=8.30 Hz), 7.15–7.24 (4H, m).

(3) Synthesis of 3-[3-(2-indanyloxy)-4-methoxyanilino]-2-cyclopenten-1-one

According to the same procedure as in Example 1(3), using 3-(2-indanyloxy)-4-methoxyaniline instead of 3-cyclopentyloxy-4-methoxyaniline, the title compound 0.53 g (yield 85.1%) was obtained as a colorless solid.

$^1$H-NMR (400 MHz, CDCl$_3$) δ 2.46–2.49 (2H, m), 2.72–2.75 (2H, m), 3.23 (2H, dd, J=16.60, 3.42 Hz), 3.38 (2H, dd, J=16.60, 6.35 Hz), 3.81 (3H, s), 5.14 (1H, m), 5.47 (1H, s), 6.54 (1H, broad s), 6.74 (1H, dd, J=8.30, 2.44 Hz), 6.79 (1H, d, J=2.44 Hz), 6.85 (1H, d, J=8.30 Hz), 7.17–7.25 (4H, m).

Example 10

Synthesis of 3-[3-(2-indanyloxy)-4-methoxyanilino]-2-methyl-2-cyclopenten-1-one (Compound No. 10 of Table 1)

2.68 g (10.52 mmole) of 3-(2-indanyloxy)-4-methoxyaniline produced in Example 9(2), 1.18 g (10.52 mmole) of 2-methyl-1,3-cyclopentanedione, and 0.07 g of p-toluenesulfonic acid were dissolved in 130 ml of toluene and the solution was heated reflux for 20 hours. After the reaction, the solvent was removed in vacuo and the residue obtained was diluted with 100 ml of methylene chloride. The organic solution was washed with water. Next, the solution was dried over anhydrous sodium sulfate, then the solvent was removed in vacuo to obtain a residue as a black-brown oil. The residue was purified by flash chromatography (SiO$^2$; eluted by 2% methanol/methylene chloride)and the solvent was removed in vacuo and the residue dried to obtain the title compound 3.60 g (yield 98.2%) as a brown solid.

$^1$H-NMR (400 MHz, CDCl$_3$) δ 1.68 (3H, s), 2.38–2.41 (2H, m), 2–57–2.58 (2H, m), 3.23 (2H, dd, J=16.60, 3.42 Hz), 3.38 (2H, dd, J=16.60, 6.83 Hz), 3.81 (3H, s), 5.15 (1H, m), 6.74–6.76 (3H, m), 6.84 (1H, d, J=9.28 Hz), 7.17–7.24 (4H, m).

Example 11

Synthesis of 3-(4-methoxy-3-phenethyloxyanilino)-2-cyclopenten-1-one (Compound No. 11 of Table 1)

(1) Synthesis of 4-methoxy-3-phenethyloxynitrobenzene

According to the same procedure as in Example 9(1), using phenethyl alcohol instead of 2-indanol, 4-methoxy-3-phenethyloxynitrobenzene (yield 100%) was obtained as a yellow solid.

$^1$H-NMR (400 MHz, CDCl$_3$) δ 3.19 (2H, t, J=7.32 Hz), 3.97 (3H, s), 4.28 (2H, t, J=7.32 Hz), 6.90 (1H, d, J=9.28 Hz), 7.27–7.36 (5H, m), 7.73 (1H, d, J=2.93 Hz), 7.91 (1H, dd, J=9.28, 2.93 Hz).

(2) Synthesis of 4-methoxy-3-phenethyloxyaniline

According to the same procedure as in Example 1(2), using 4-methoxy-3-phenetyloxynitrobenzene instead of 3-cyclopenthyloxy-4-methoxynitrobenzene, 4-methoxy-3-phenethyloxyaniline was obtained as a brown oil.

$^1$H-NMR (400 MHz, CDCl$_3$) δ 3.15 (2H, t, J=7.33 Hz), 3.77 (3H, s), 4.16 (2H, t, J=7.33 Hz), 6.23 (1H, dd, J=8.30, 2.44 Hz), 6.30 (1H, d, J=2.44 Hz), 6.72 (1H, d, J=8.30 Hz), 7.21–7–33 (5H, m).

(3) Synthesis of 3-(4-methoxy-3-phenethyloxyanilino)-2-cyclopenten-1-one

According to the same procedure as in Example 1(3), using 4-methoxy-3-phenethyloxyaniline instead of 3-cyclopentyloxy-4-methoxyaniline, the title compound (yield 87.9%) was obtained as a yellow solid.

$^1$H-NMR (400 MHz, CDCl$_3$) δ 2.41 (2H, m), 2.69 (2H, m), 3.14 (2H, t, J=7.32 Hz), 3.84 (3H, s), 4.14 (2H, t, J=7.32 Hz), 5.41 (1H, s), 6.70 (2H, m), 6.82 (1H, d, J=7.81 Hz), 7.22–7.32 (5H, m).

Example 12

Synthesis of 3-(4-methoxy-3-phenethyloxyanilino)-2-methyl-2-cyclopenten-1-one (Compound No. 12 of Table 1)

According to the same procedure as in Example 4, using 4-methoxy-3-phenethyloxyaniline produced in Example 11(2) instead of 3-cyclopentyloxy-4-methoxyaniline, the title compound (yield 74.2%) was obtained as a brown solid.

$^1$H-NMR (400 MHz, CDCl$_3$) δ 1.64 (3H, s), 2.35 (2H, m), 2.51 (2H, m), 3.16 (1H, t, J=7.32 Hz), 3.87 (3H, s), 4.18 (1H, t, J=7.32 Hz), 6.67 (1H, d, J=2.44 Hz), 6.72 (1H, dd, J=8.79, 2.44 Hz), 6.61–6.77 (1H, broad), 6.84 (1H, d, J=8.79 Hz), 7.23–7.33 (5H, m).

Example 13

Synthesis of 3-(3-cyclohexyloxy-4-methoxyanilino)-2-cyclopenten-1-one (Compound No. 13 of Table 1)

(1) Synthesis of 3-cyclohexyloxy-4-methoxynitrobenzene

According to the same procedure as in Example 9(1), using cyclohexanol instead of 2-indanol, 3-cyclohexyloxy-4-methoxynitrobenzene (yield 49.2%) was obtained as a yellow solid.

¹H-NMR (400 MHz, CDCl₃) δ 1.39–1.43 (3H, m), 1.56–1.64 (3H, m), 1.83–1.87 (2H, m), 2.04–2.07 (2H, m), 3.95 (3H, s), 4.32 (1H, m), 6.91 (1H, d, J=8.79 Hz), 7.76 (1H, d, J=2.44 Hz), 7.89 (1H, dd, J=8.79, 2.44 Hz).

(2) Synthesis of 3-cyclohexyloxy-4-methoxyaniline

According to the same procedure as in Example 1(2), using 3-cyclohexyloxy-4-methoxynitrobenzene instead of 3-cyclopentyloxy-4-methoxynitrobenzene, 3-cyclohexyloxy-4-methoxyaniline was obtained as a brown oil.

¹H-NMR (400 MHz, CDCl₃) δ 1.25–1.37 (3H, m), 1.50–1.58 (3H, m), 1.80 (2H, m), 2.01 (2H, m), 3.41 (2H, broad s), 3.77 (3H, s), 4.13 (1H, m), 6.24 (1H, dd, J=8.30, 2.44 Hz), 6.35 (1H, d, J=2.44 Hz), 6.71 (1H, d, J=8.30 Hz).

(3) Synthesis of 3-(3-cyclohexyloxy-4-methoxyanilino)-2-cyclopenten-1-one

According to the same procedure as in Example 1(3), using 3-cyclohexyloxy-4-methoxyaniline instead of 3-cyclopentyloxy-4-methoxyaniline, the title compound (yield 65.1%) was obtained as a yellow solid.

¹H-NMR (400 MHz, CDCl₃) δ 1.31–1.36 (3H, m), 1.53–1.60 (3H, m), 1.80 (2H, m), 2.00 (2H, m), 2.46 (2H, m), 2.72 (2H, m), 3.85 (3H, s), 4.16 (1H, m), 5.44 (1H, s), 6.56 (1H, broad s), 6.71 (1H, dd, J=8.79, 1.96 Hz), 6.76 (1H, d, J=1.96 Hz), 6.84 (1H, d, J=8.79 Hz).

Example 14

Synthesis of 3-(3-cyclohexyloxy-4-methoxyanilino)-2-methyl-2-cyclopenten-1-one (Compound No. 14 of Table 1)

According to the same procedure as in Example 4, using 3-cyclohexyloxy-4-methoxyaniline produced in Example 13(2) instead of 3-cyclopentyloxy-4-methoxyaniline, the title compound (yield 86.0%) was obtained as a brown solid.

¹H-NMR (400 MHz, CDCl³) δ 1.26–1.37 (3H, m), 1.56–1.61 (3H, m), 1.68 (3H, s), 1.82 (2H, m), 2.00–2.05 (2H, m), 2.38–2.41 (2H, m), 2.55 (2H, m), 3.86 (3H, s), 4.18 (1H, m), 6.45 (1H, broad s), 6.71–6.73 (2H, m), 6.84 (1H, d, J=9.28 Hz).

Example 15

Synthesis of 3-(3-cyclopropylmethoxy-4-methoxyanilino)-2-cyclopneten-1-one (Compound No. 15 of Table 1)

(1) Synthesis of 3-cyclopropylmethoxy-4-methoxynitrobenzene

According to the same procedure as in Example 9(1), using cyclopropylcarbinol instead of 2-indanol, 3-cyclopropylmethoxy-4-methoxynitrobenzene (yield 89.0%) was obtained as a light yellow solid.

¹H-NMR (400 MHz, CDCl₃) δ 0.40 (2H, m), 0.70 (2H, m), 1.36 (1H, m), 3.93 (2H, d, J=7.33 Hz), 3.98 (3H, s), 6.91 (1H, d, J=8.79 Hz), 7.73 (1H, d, J=2.44 Hz), 7.90 (1H, dd, J=8.79, 2.44 Hz).

(2) Synthesis of 3-cyclopropylmethoxy-4-methoxyaniline

According to the same procedure as in Example 1(2), using 3-cyclopropylmethoxy-4-methoxynitrobenzene instead of 3-cyclopentyloxy-4-methoxynitrobenzene, 3-cyclopropylmethoxy-4-methoxyaniline was obtained as a purple oil.

¹H-NMR (400 MHz, CDCl₃) δ 0.32 (2H, m), 0.62 (2H, m), 1.30 (1H, m), 3.76 (2H, d, J=7.33 Hz), 3.79 (3H, s), 3.96 (2H, broad s), 6.25 (1H, dd, J=8.30, 2.44 Hz), 6.32 (1H, d, J=2.44 Hz), 6.69 (1H, d, J=8.30 Hz).

(3) Synthesis of 3-(3-cyclopropylmethoxy-4-methoxyanilino)-2-cyclopenten-1-one

According to the same procedure as in Example 1(3), using 3-cyclopropylmethoxy-4-methoxyaniline instead of the 3-cyclopentyloxy-4-methoxyaniline, the title compound (yield 81.1%) was obtained as a pale yellow solid.

¹H-NMR (400 MHz, CDCl₃) δ 0.35 (2H, m), 0–65 (2H, m), 1.32 (1H, m), 2.46 (2H, m), 2.73 (2H, m), 3.80 (2H, d, J=6.84 Hz), 3.87 (3H, s), 5.44 (1H, s), 6.70 (1H, dd, J=8.30, 2.44 Hz), 6.74 (1H, d, J=2.44 Hz), 6.76–6.88 (1H, broad s), 6.83 (1H, d, J=8.30 Hz).

Example 16

Synthesis of 3-(3-cyclopropylmethoxy-4-methoxyanilino)-2-methyl-2-cyclogenten-1-one (Compound No. 16 of Table 1)

According to the same procedure as in Example 4, using 3-cyclopropylmethoxy-4-methoxyaniline produced in Example 15(2) instead of 3-cyclopentyloxy-4-methoxyaniline, the title compound (yield 94.4%) was obtained as a black solid.

¹H-NMR (400 MHz, CDCl₃) δ 0.35–0.38 (2H, m), 0.64–0.69 (2H, m), 1.34 (1H, m), 1.67 (3H, s), 2.38–2.40 (2H, m), 2.55 (2H, m), 3.84 (2H, d, J=7.32 Hz), 3.89 (3H, s), 6.43 (1H, broad s), 6.69 (1H, d, J=2.44 Hz), 6.73 (1H, dd, J=8.30, 2.44 Hz), 6.85 (1H, d, J=8.30 Hz).

Example 17

Synthesis of 3-(3-butoxy-4-methoxyanilino)-2-cyclopenten-1-one (Compound No. 17 of Table 1)

(1) Synthesis of 3-butoxy-4-methoxynitrobenzene

According to the same procedure as in Example 1(1), using butyl iodide instead of the bromocyclopentane, 3-butoxy-4-methoxynitrobenzene (yield 100%) was obtained as a yellow solid.

¹H-NMR (400 MHz, CDCl₃) δ 1.00 (3H, t, J=7.33 Hz), 1.52 (2H, m), 1.87 (2H, m), 3.97 (3H, s), 4.09 (2H, t, J=6.83 Hz), 6.90 (1H, d, J=8.79 Hz), 7.74 (1H, d, J=2.93 Hz), 7.90 (1H, dd, J=8.79, 2.93 Hz).

(2) Synthesis of 3-butoxy-4-methoxyaniline

According to the same procedure as in Example 1(2), using 3-butoxy-4-methoxynitrobenzene instead of the 3-cyclopentyloxy-4-methoxynitrobenzene, 3-butoxy-4-methoxyaniline was obtained as a purple oil.

¹H-NMR (400 MHz, CDCl₃) δ 0.96 (3H, t, J=7.32 Hz), 1.48 (2H, m), 1.80 (2H, m), 3.45 (2H, broad s), 3.77 (3H, s), 3.94 (2H, t, J=6.84 Hz), 6.20 (1H, dd, J=8.30, 2.44 Hz), 6.30 (1H, d, J=2.44 Hz), 6.69 (1H, d, J=8.30 Hz).

(3) Synthesis of 3-(3-butoxy-4-methoxyanilino)-2-cyclopenten-1-one

According to the same procedure as in Example 1(3), using 3-butoxy-4-methoxyaniline instead of 3-cyclopentyloxy-4-methoxyaniline, the title compound (yield 81.6%) was obtained as a pale yellow solid.

¹H-NMR (400 MHz, CDCl₃) δ 0.98 (3H, t, J=7.33 Hz), 1.49 (2H, m), 1.82 (2H, m), 2.45–2.47 (2H, m), 2.71–2.74 (2H, m), 3.97 (2H, t, J=6.83 Hz), 5.46 (1H, s), 6.69 (1H, dd, J=8.79, 2.44 Hz), 6.72–6.80 (1H, broad), 6.74 (1H, d, J=2.44 Hz), 6.83 (1H, d, J=8.79 Hz).

Example 18

Synthesis of 3-(3-butoxy-4-methoxyanilino)-2-methyl-2-cyclopenten-1-one (Compound No. 18 of Table 1)

According to the same procedure as in Example 4, using 3-butoxy-4-methoxyaniline produced in Example 17(2)

instead of 3-cyclopentyloxy-4-methoxyaniline, the title compound (yield 66.2%) was obtained as a brown solid.

$^1$H-NMR (400 MHz, CDCl$_3$) δ 0.98 (3H, t, J=7.33 Hz), 1.50 (2H, m), 1.67 (3H, s), 1.84 (2H, m), 2.38–2.40 (2H, m), 2.55–2.56 (2H, n), 3.87 (3H, s), 4.00 (2H, t, J=6.83 Hz), 6.51 (1H, broad s), 6.70 (1H, d, J=2.44 Hz), 6.72 (1H, dd, J=8.30, 2.44 Hz), 6.84 (1H, d, J=8.30 Hz)

Example 19

Synthesis of 3-[3-(2-indanyloxy)-4-methoxyanilino]-2-cyclohexen-1-one (Compound No. 19 of Table 1)

(1) Synthesis of 3-(3-hydroxy-4-methoxyanilino)-2-cyclohexen-1-one

A solution of 1.00 g (7.19 mmole) of 3-hydroxy-4-methoxyaniline, 0.83 g (7.19 mmole) of 1,3-cyclohexanedione, and 50 mg of p-toluenesulfonic acid in 20 ml of benzene were heated reflux for 4.5 hours. The reaction solution was allowed to stand for one night at room temperature and the precipitated brown solid was collected by suction filtration. The crystal was washed with benzene, then was dried in vacuo to obtain 3-(3-hydroxy-4-methoxyanilino)-2-cyclohexen-1-one 1.68 g (yield 100%).

$^1$H-NMR (400 MHz, CDCl$_3$) δ 2.04 (2H, m), 2.36 (2H, t, J=6.35 Hz), 2.47 (2H, t, J=6.35 Hz), 3.89 (3H, s), 5.47 (1H, s), 5.65–5.90 (2H, broad), 6.67 (1H, dd, J=8.30, 2.44 Hz), 6.75 (1H, d, J=2.44 Hz), 6.79 (1H, d, J=8.30 Hz).

(2) Synthesis of 3-[3-(2-indanyloxy)-4-methoxyanilino]-2-cyclohexen-1-one

According to the same procedure as in Example 9(1), using 3-(3-hydroxy-4-methoxyanilino)-2-cyclohexen-1-one instead of 2-methoxy-5-nitrophenol, the title compound (yield 54.4%) was obtained as a brown solid.

$^1$H-NMR (400 MHz, CDCl$_3$) δ 2.02–2.08 (2H, m), 2.37 (2H, t, J=6.35 Hz), 2.48 (2H, t, J=6.35 Hz), 3.22 (2H, dd, J=16.61, 3.91 Hz), 3.36 (2H, dd, J=16.61, 6.35 Hz), 3.80 (3H, s), 5.14 (1H, m), 5.44 (1H, s), 5.91 (1H, broad s), 6.74–6.76 (2H, m), 6.82–6.84 (1H, m), 7.16–7.19 (2H, m), 7.22–7.25 (2H, m).

Example 20

Synthesis of 3-(3-benzyloxy-4-methoxyanilino)-2-cyclohexen-1-one (Compound No. 20 of Table 1)

According to the same procedure as in Example 19(2), using benzyl alcohol instead of 2-indanol, the title compound (yield 68.0%) was obtained as a brown solid.

$^1$H-NMR (400 MHz, CDCl$_3$) δ 2.01 (2H, m, J=6.35 Hz), 2.34 (2H, t, J=6.35 Hz), 2.42 (2H, t, J=6.35 Hz), 3.88 (3H, s), 5.11 (2H, s), 5.39 (1H, s), 5.87 (1H, broad s), 6.70 (1H, d, J=2.44 Hz), 6.74 (1H, dd, J=8.79, 2.44 Hz), 6.84 (1H, d, J=8.79 Hz), 7.29–7.43 (5H, m).

Example 21

Synthesis of 4-(3-cyclopentyloxy-4-methoxyanilino)-1,2,5,6-tetrahydropyridin-2-one (Compound No. 21 of Table 1)

0.60 g (2.89 mmole) of the 3-cyclopentyloxy-4-methoxyaniline produced in Example 1(2) and 0.33 g (2.89 mmole) of 2, 4-dioxopiperidine were dissolved in solution of 15 ml of benzene, 4 ml of acetonitrile, and 1 ml of methanol and the mixture was stirred at room temperature for 24 hours. After the reaction, the solvent was removed in vacuo and the residue was triturated with ether. The precipitated brown crystal was collected by filtration, then dried in vacuo to obtain the title compound 0.88 g (yield 100%).

$^1$H-NMR (400 MHz, CDCl$_3$) δ 1.58–1.62 (2H, m), 1.78–1.93 (6H, m), 2.51 (2H, t, J=6.84 Hz), 3.44 (2H, ddd, J=6.84, 6.84, 2.44 Hz), 3.83 (3H, s), 4.72 (1H, m), 5.12 (1H, s), 5.34 (1H, broad), 5.83 (1H, broad s), 6.69 (1H, dd, J=8.30, 1.95 Hz), 6.71 (1H, d, J=1.95 Hz), 6.80 (1H, d, J=8.30 Hz).

Example 22

Synthesis of 1-benzyl-4-(3-cyclopentyloxy-4-methoxyanilino)-1,2,5,6-tetrahydropyridin-2-one (Compound No. 22 of Table 1)

0.50 g (2.41 mmole) of 3-cyclopentyloxy-4-methoxyaniline produced in Example 1(2) and 0.49 g (2.41 mmole) of 1-benzyl-2,4-dioxopiperidine were dissolved in 20 ml of benzene and the mixture was stirred at room temperature for 20 hours. After the reaction, the precipitated crystal was collected by filtration and washed with benzene, then was dried in vacuo to obtain the title compound 0.76 g (yield 80.6%) as a light pink solid.

$^1$H-NMR (400 MHz, CDCl$_3$) δ 1.55–1.63 (2H, m), 1.81–1.96 (6H, m), 2.46 (2H, t, J=6.84 Hz), 3.33 (2H, t, J=6.84 Hz), 3.84 (3H, 5), 4.63 (2H, s), 4.74 (1H, m), 5.25 (1H, s), 5.40 (1H, broad s), 6.67–6.71 (2H, m), 6.80 (1H, d, J=8.30 Hz), 7.28–7.37 (5H, m).

Example 23

Synthesis of 4-[3-[3-[(1RS,2RS, 4SR)-bicyclo [2.2.1]hepta-2-yloxy]-4-methoxyanilino]-1,2,5,6-tetrahydropyridin-2-one (Compound No. 23 of Table 1)

According to the same procedure as in Example 21, using 3-[(1RS,2RS,4SR)-bicyclo[2.2.1]hept-2-yloxy]-4-methoxyaniline produced in Example 8(2) instead of 3-cyclopentyloxy-4-methoxyaniline, the title compound (yield 74.3%) was obtained as a light brown solid.

$^1$H-NMR (400 MHz, CDCl$_3$) δ 1.12–1.22 (3H, m), 1.49–1.62 (3H, m), 1.73–1.78 (2H, m), 2.33 (1H, m), 2.49–2.53 (3H, m), 3.45–3.50 (2H, m), 3.83 (3H, s), 4.15 (1H, m), 5.05 (1H, broad s), 5.12 (1H, s), 5.52 (1H, broad s), 6.65 (1H, d, J=2.44 Hz), 6.69 (1H, dd, J=8.30, 2.44 Hz), 6.81 (1H, d, J=8.30 Hz).

Example 24

Synthesis of 3-(3-cyclopentyloxy-4-methoxyanilino)-2-dimethylaminomethyl-2-cyclopenten-1-one (Compound No. 24 of Table 1)

0.16 g (1.91 mmole) of dimethylamine hydrochloride and 0.18 g (2.09 mmole) of 35% aqueous solution of formaldehyde were dissolved in 2 ml of benzene. To this solution was carefully dropwise added at room temperature a solution of 0.50 g (1.74 mmole) of the 3-(3-cyclopentyloxy-4-methoxyanilino)-2-cyclopenten-1-one obtained in Example 1 in 15 ml of a benzene-methanol (1:2). The solution was stirred at room temperature for one night, then the solvent was removed in vacuo to obtain a residue as a light yellow solid. The residue was purified by flash chromatography. The solvent was removed in vacuo and the residue dried to obtain the title compound 0.55 g (yield 92.2%) as a colorless solid.

$^1$H-NMR (400 MHz, CDCl$_3$) δ 1.60–1.63 (2H, m), 1.82–1.89 (4H, m), 1.96–1.99 (2H, m), 2.41–2.44 (2H, m), 2.68–2.72 (8H, m), 3.77 (2H, s), 3.84 (3H, s), 4.75–4.78 (1H, m), 6.81 (2H, s), 6.94 (1H, s).

Example 25

Synthesis of 3-(3-cyclopentyloxy-4-methoxyanilino)- 2-(4-morpholinomethyl)-2-cyclopenten-1-one (Compound No. 25 of Table 1)

According to the same procedure as in Example 24, using morpholine instead of the dimethylamine hydrochloride, the title compound (yield 29.2%) was obtained as a colorless solid.

$^1$H-NMR (400 MHz, CDCl$_3$) δ 1.64–1.95 (8H, m), 2.40–2.43 (2H, m), 2.51 (4H, broad s), 2.67 (2H, m), 3.37 (2H, s), 3.75 (4H, broad s), 3.85 (3H, s), 4.74–4.76 (1H, m), 6.61–6.63 (2H, m), 6.84 (1H, d, J=8.79 Hz), 9.66 (1H, broad s).

Example 26

Synthesis of 3-(3-cyclopentyloxy-4-methoxy-N-methylanilino)-2-cyclopenten-1-one (Compound No. 26 of Table 1)

0.10 g (0.35 mmole) of 3-(3-cyclopentyloxy-4-methoxyanilino)-2-cyclopenten-1-one produced in Example 1, 0.02 g of sodium hydride (60%), and 0.06 g (0.42 mmole) of methyl iodide were dissolved in 4 ml of N,N-dimethylformamide and the solution was stirred at room temperature for one night. The reaction solution was quenched with water, then was extracted with methylene chloride. The extract was dried over anhydrous magnesium sulfate, and the solvent was removed in vacuo to obtain a crude product. The crude product was purified by flash chromatography (SiO$_2$; eluted by 2% methanol/methylene chloride) to obtain the title compound 0.10 g (yield 93.4%) as a colorless solid.

$^1$H-NMR (400 MHz, CDCl$_3$) δ 1.61–1.64 (2H, m), 1.80–1.97 (6H, m), 2.40 (4H, m), 3.30 (3H, s), 3.86 (3H, s), 4.72–4.76 (1H, m), 5.11 (1H, broad s), 6.70 (1H, d, J=1.95 Hz), 6.73 (1H, dd, J=8.31, 1.95 Hz), 6.86 (1H, d, J=8.31 Hz).

Example 27

Synthesis of 3-(3-cyclopentyloxy-4-methoxy-N-methylanilino)-2-cyclohexen-1-one (Compound No. 27 of Table 1)

According to the same procedure as in Example 26, using 3-(3-cyclopentyloxy-4-methoxyanilino)-2-cyclohexen-1-one produced in Example 2 instead of 3-(3-cyclopentyloxy-4-methoxyanilino)-2-cyclopenten-1-one, the title compound (yield 53.6%) was obtained as a brown solid.

$^1$H-NMR (400 MHz, CDCl$_3$) δ 1.61–1.64 (2H, m), 1.81–1.95 (8H, m), 2.21 (2H, t, J=6.35 Hz), 2.30 (2H, t, J=6.34 Hz), 3.20 (3H, s), 3.86 (3H, s), 4.72–4.75 (1H, m), 5.30 (1H, s), 6.61 (1H, d, J=2.44 Hz), 6.66 (1H, dd, J=8.30, 2.44 Hz), 6.84 (1H, d, J=8.30 Hz).

Example 28

Synthesis of 3-[3-cyclopentyloxy-4-methoxy-N-(4-pyridylmethyl)anilino]-2-cyclopenten-1-one (Compound No. 28 of Table 1)

According to the same procedure as in Example 26, using 4-(chloromethyl)pyridine hydrochloride instead of methyl iodide, the title compound (yield 66.7%) was obtained as a brown solid.

$^1$H-NMR (400 MHz, CDCl$_3$) δ 1.71 (2H, m), 1.75–1.82 (6H, m), 2.42 (2H, broad s), 2.52 (2H, broad s), 3.84 (3H, s), 4.63–4.64 (1H, m), 4.77 (2H, s), 5.19 (1H, broad s), 6.59 (1H, d, J=2.44 Hz), 6.69 (1H, dd, J=8.79, 2.44 Hz), 6.81 (1H, d, J=8.79 Hz), 7.17 (2H, m), 8.58 (2H, m).

Example 29

Synthesis of 3-(N-acetyl-3-cyclopentyloxy-4-methoxyanilino)-2-cyclopenten-1-one (Compound No. 29 of Table 1)

According to the same procedure as in Example 26, using acetyl chloride instead of methyl iodide, the title compound (yield 77.6%) was obtained as a colorless solid.

$^1$H-NMR (400 MHz, CDCl$_3$) δ 1.59–1.63 (2H, m), 1.85–1.95 (6H, m), 1.98 (3H, s), 2.38–2.40 (2H, m), 2.97–2.99 (2H, m), 3.89 (3H, s), 4.74 (1H, m), 5.69 (1H, s), 6.70 (1H, d, J=2.44 Hz), 6.76 (1H, dd, J=8.30, 2.44 Hz), 6.92 (1H, d, J=8.30 Hz).

Example 30

Synthesis of 3-(N-benzyl-3-cyclopentyloxy-4-methoxyanilino)-2-cyclopenten-1-one (Compound No. 30 of Table 1)

According to the same procedure as in Example 26, using benzyl bromide instead of methyl iodide, the title compound (yield 87.9%) was obtained as a brown oil.

$^1$H-NMR (400 MHz, CDCl$_3$) δ 1.56–1.59 (2H, m), 1.73–1.79 (6H, m), 2.40 (4H, broad s), 3.83 (3H, s), 4.58 (1H, m), 4.76 (2H, s), 5.27 (1H, broad s), 6.53 (1H, d, J=2.44 Hz), 6.67 (1H, dd, J=8.30, 2.44 Hz), 6.79 (1H, d, J=8.30 Hz), 7.19–7.32 (5H, m).

Example 31 synthesis of 3-(3-cyclopentyloxy-4-methoxyanilino)-2-ethyl-2-cyclopenten-1-one (Compound No. 31 of Table 1)

According to the same procedure as in Example 1(3), using 2-ethyl-1,3-cyclopentanedione instead of 1,3-cyclopentanedione, the title compound (yield 94.1%) was obtained as a brown solid.

$^1$H-NMR (400 MHz, CDCl$_3$) δ 1.05 (3H, t, J=7.33 Hz), 1.61–1.66 (2H, m), 1.82–1.96 (6H, m), 2.22 (2H, q, J=7.33 Hz), 2.36–2.39 (2H, m), 2.55 (2H, t, J=4.88 Hz), 3.86 (3H, s), 4.74–4.77 (1H, m), 6.48 (1H, broad s), 6–69–6.71 (2H, m), 6.83 (1H, d, J=8.79 Hz).

Example 32

Synthesis of 2-ethyl-3-[3-(2-indanyloxy)-4-methoxyanilino]-2-cyclopenten-1-one (Compound No. 32 of Table 1)

According to the same procedure as in Example 9, using 2-ethyl-1,3-cyclopentanedione instead of 1,3-cyclopentanedione, the title compound (yield 91.5%) was obtained as a brown solid.

$^1$H-NMR (400 MHz, CDCl$_3$) δ 1.06 (3H, t, J=7.32 Hz), 2.22 (2H, q, J=7.32 Hz), 2.38–2.41 (2H, m), 2.57–2.58 (2H, m), 3.25 (2H, dd, J=16.60, 3.90 Hz), 3.39 (2H, dd, J=16.60, 6.34 Hz), 3.83 (3H, s), 5.16–5.20 (1H, m), 6.44 (1H, broad s), 6.74–6.77 (2H, m), 6.84–6.87 (1H, m), 7.18–7.25 (4H, m).

Example 33

Synthesis of 2-benzyl-3-(3-cyclopentyloxy-4-methoxyanilino)-2-cyclopenten-1-one (Compound No. 33 of Table 1)

According to the same procedure as in Example 1(3), using 2-benzyl-1,3-cyclopentanedione instead of 1,3- cyclopentanedione, the title compound (yield 96.5%) was obtained as a brown solid.

$^1$H-NMR (400 MHz, CDCl$_3$) δ 1.62–1.91 (8H, m), 2.44–2.47 (2H, m), 2.57–2.59 (2H, m), 3.62 (2H, 5), 3.81 (3H, s), 4.64–4.66 (1H, m), 6.32 (1H, s), 6.40 (1H, d, J=2.44 Hz), 6.46 (1H, dd, J=8.30, 2.44 Hz), 6.75 (1H, d, J=8.30 Hz), 7.22–7.33 (5H, m).

Example 34

Synthesis of 3-[3-[2-(2-indanyl)ethoxy]-4-methoxyanilino]-2-cyclopenten-1-one (Compound No. 34 of Table 1)

(1) Synthesis of 3-[2-(2-indanyl)ethoxy]-4-methoxynitrobenzene

According to the same procedure as in Example 9(1), using 2-(2-indanyl)ethanol instead of 2-indanol, 3-[2-(2-indanyl)ethoxy]-4-methoxynitrobenzene (yield 97.2%) was obtained as a yellow solid.

$^1$H-NMR (400 MHz, CDCl$_3$) δ 2.12 (2H, q, J=6.83 Hz), 2.68–2.74 (3H, m), 3.11–3.17 (2H, m), 3.97 (3H, s), 4.18 (2H, t, J=6.83 Hz), 6.91 (1H, d, J=9.27 Hz), 7.13–7.16 (2H, m), 7.19–7.22 (2H, m), 7.77 (1H, d, J=2.93 Hz), 7.92 (1H, dd, J=9.27, 2.93 Hz).

(2) Synthesis of 3-[3-[2-(2-inidanyl)ethoxy]-4-methoxyanilino]-2-cyclopenten-1-one According to the same procedure as in Example 1(2), using 3-[2-(2-indanyl)ethoxy]-4-methoxynitrobenzene instead of 3-cyclopentyloxy-4-methoxynitrobenzene, 3-[2-(2-indanyl)ethoxy)-4-methoxyaniline was obtained as a pink solid. Next, according to the same procedure as in Example 1(3), using 3-[2-(2-indanyl)ethoxy]-4-methoxyaniline instead of 3-cyclopentyloxy-4-methoxyaniline, the title compound (yield 97.7%) was obtained as a pale brown solid.

$^1$H-NMR (400 MHz, CDCl$_3$) δ 2.08 (2H, q, J=6.35 Hz), 2.47–2.50 (2H, m), 2.65–2.75 (5H, m), 3.09–3.13 (2H, m), 3.87 (3H, s), 4.06 (2H, t, J=6.35 Hz), 5.48 (1H, s), 6.47 (1H, broad s), 6.72 (1H, dd, J=8.30, 2.44 Hz), 6.76 (1H, d, J=2.44 Hz), 6.85 (1H, d, J=8.30 Hz), 7.12–7.15 (2H, m), 7.18–7.22 (2H, m).

Example 35

Synthesis of 3-[3-[2-(2-indanyl)ethoxy]-4-methoxyanilino]-2-methyl-2-cyclopenten-1-one (Compound No. 35 of Table 1)

According to the same procedure as in Example 10, using 3-[2-(2-indanyl)ethoxy]-4-methoxyaniline produced in Example 34(2) instead of 3-(2-indanyloxy)-4-methoxyaniline, the title compound (yield 96.3%) was obtained as a brown solid.

$^1$H-NMR (400 MHz, CDCl$_3$) δ 1.68 (3H, s), 2.08 (2H, m), 2.39–2.40 (2H, m), 2.56 (2H, m), 2.67–2.70 (3H, m), 3.11–3.13 (2H, m), 3.87 (3H, s), 4.08 (2H, t, J=6.83 Hz), 6.63 (1H, broad s), 6.72–6.74 (2H, m), 6.84 (1H, d, J=8.78 Hz), 7.12–7.14 (2H, m), 7.18–7.20 (2H, m).

Example 36

Synthesis of 3-[4-methoxy-3-(3-2,3,4,5-tetrahydrofuranyloxy)anilino]-2-cyclopenten-1-one (Compound No. 36 of Table 1)

(1) Synthesis of 4-methoxy-3-(3-2,3,4,5-tetrahydrofuranyloxy)nitrobenzene

According to the same procedure as in Example 9(1), using 3-hydroxy-2,3,4,5-tetrahydrofuran instead of 2-indanol, 4-methoxy-3-(3–2,3,4,5-tetrahydrofuranyloxy) nitrobenzene (yield 84.2%) was obtained as a pale orange solid.

$^1$H-NMR (400 MHz, CDCl$_3$) δ 2.17–2.23 (1H, m), 2.25–2.35 (1H, m), 3.91–3.95 (1H, m), 3.96 (3H, s), 3.98–4.07 (3H, m), 5.02 (1H, m), 6.93 (1H, d, J=8.79 Hz), 7.70 (1H, d, J=2.45 Hz), 7.94 (1H, dd, J=8.79, 2.45 Hz).

(2) Synthesis of 3-[4-methoxy-3-(3-2,3,4,5-tetrahydrofuranyloxy)anilino]2-cyclopenten-1-one According to the same procedure as in Example 1(2), using 4-methoxy-3-(3-2,3,4,5-tetrahydrofuranyloxy)nitrobenzene instead of 3-cyclopentyloxy-4-methoxynitrobenzene, 4-methoxy-3-( 3-2,3,4,5-tetrahydrofuranyloxy)aniline was obtained as a purple solid. Next, according to the same produce as in Example 1(3), using 4-methoxy-3-(3-2,3,4,5-tetrahydrofuranyloxy)aniline instead of 3-cyclopentyloxy-4-methoxyaniline, the title compound (yield 87.4%) was obtained as a pale yellow solid.

$^1$H-NMR (400 MHz, CDCl$_3$) δ 2.17–2.21 (2H, m), 2.47–2.50 (2H, m), 2.73–2.75 (2H, m), 3.85 (3H, s), 3.87–3.93 (1H, m), 3.96–4.06 (3H, m), 4.91 (1H, m), 5.44 (1H, s), 6.47 (1H, broad s), 6.69 (1H, d, J=2.44 Hz), 6.76 (1H, dd, J=8.30, 2.44 Hz), 6.87 (1H, d, J=8.30 Hz).

Example 37

Synthesis of 3-[4-methoxy-3-(3-2,3,4,5-tetrahydrofuranyloxy)anilino]-2-methyl-2-cyclopenten-1-one (Compound No. 37 of Table 1)

According to the same procedure as in Example 10, using 4-methoxy-3-(3-2,3,4,5-tetrahydrofuranyloxy)aniline produced in Example 36(2) instead of 3-(2-indanyloxy)-4-methoxyaniline, the title compound (yield 67.5%) was obtained as a dark purple solid.

$^1$H-NMR (400 MHz, CDCl$_3$) δ 1.68 (3H, s), 2.18–2.22 (2H, m), 2.39–2.41 (2H, m), 2.56 (2H, m), 3.87 (3H, s), 3.89–3.94 (1H, m), 3.97–4.07 (3H, m), 4.94 (1H, m), 6.47 (1H, broad s), 6.67 (1H, d, J=1.96 Hz), 6.77 (1H, dd, J=8.30, 1.96 Hz), 6.87 (1H, d, J=8.30 Hz).

Example 38

Synthesis of 3-(3-cyclopentyloxy-4-methoxyanilino)-6,6-dimethyl-2-cyclohexen-1-one (Compound No. 38 of Table 1)

According to the same procedure as in Example 1, using 4,4-dimethyl-1,3-cyclohexanedione instead of 1,3-cyclopentanedione, the title compound (yield 93.6%) was obtained as a colorless solid.

$^1$H-NMR (400 MHz, CDCl$_3$) δ 1.15 (6H, s), 1.56–1.62 (2H, m), 1.80–1.94 (6H, m), 1.87 (2H, t, J=6.35 Hz), 2.49 (2H, t, J=6.35 Hz), 3.83 (3H, 5), 4.72 (1H, m), 5.33 (1H, s), 5.78 (1H, broad s), 6.68–6.71 (2H, m), 6.80 (1H, d, J=7.81 Hz).

Example 39

Synthesis of 3-(3-cyclopentyloxy-4-methoxyanilino)-5-phenyl-2-cyclohexen-1-one (Compound No. 39 of Table 1)

According to the same procedure as in Example 1, using 5-phenyl-1,3-cyclohexanedione instead of 1,3-cyclopentanedione, the title compound (yield 87.0%) was obtained as a pale yellow solid.

$^1$H-NMR (400 MHz, CDCl$_3$) δ 1.60–1.63 (2H, m), 1.81–2.05 (6H, m), 2.53–2.63 (3H, m), 2.83 (1H, dd, J=16.11, 12.21 Hz), 3.43 (1H, m), 3.84 (3H, s), 4.73 (1H, m), 5.50 (1H, s), 5.95 (1H, broad s), 6.70–6.72 (2H, m), 6.81–6.83 (1H, m), 7.27–7.29 (3H, m), 7.35–7.39 (2H, m).

Example 40

Synthesis of 3-(3-cyclyopentylmethoxy-4-methoxyanilino)-2-cyclopenten-1-one (Compound No. 40 of Table 1)

(1) Synthesis of 3-(3-cyclopentylmethoxy-4-methoxynitrobenzene

According to the same procedure as in Example 9(1), using cyclopentylmethanol instead of 2-indanol, 3-cyclopentylmethoxy-4-methoxynitrobenzene (yield 98.6%) was obtained as a yellow solid.

$^1$H-NMR (400 MHz, CDCl$_3$) δ 1.34–1.43 (2H, m), 1.55–1.69 (4H, m), 1.85–1.92 (2H, m), 2.47 (1H, m, J=7.32 Hz), 3.95 (2H, d, J=7.32 Hz), 3.96 (3H, s), 6.90 (1H, d, J=8.79 Hz), 7.74 (1H, d, J=2.93 Hz), 7.90 (1H, dd, J=8.79, 2.93 Hz).

(2) Synthesis of 3-(3-cyclopentylmethoxy-4-methoxyanilino)-2-cyclopenten-1-one

According to the same procedure as in Example 1(2), using 3-cyclopentylmethoxy-4-methoxynitrobenzene instead of 3-cyclopentyloxy-4-methoxynitrobenzene, 3-cyclopentylmethoxy-4-methoxyaniline was obtained as a purple oil. Next, according to the same procedure as in Example 1(3), using 3-cyclopentylmethoxy-4-methoxyaniline instead of 3-cyclopentyloxy-4-methoxyaniline, the title compound (yield 97.1%) was obtained as a pale yellow solid.

$^1$H-NMR (400 MHz, CDCl$_3$) δ 1.31–1.40 (2H, m), 1.55–1.70 (4H, m), 1.83–1.90 (2H, m), 2.40–2–49 (3H, m), 2.73 (2H, m), 3.83 (2H, d, J=7.32 Hz), 3.86 (3H, s), 5.47 (1H, s), 6.53 (1H, broad s), 6.69 (1H, dd, J=8.79, 1.96 Hz), 6.74 (1H, d, J=1.96 Hz), 6.84 (1H, d, J=8.79 Hz).

Example 41

Synthesis of 3-(3-cyclopentylmethoxy-4-methoxyanilino)-2-methyl-2-cyclopenten-1-one (Compound No. 41 of Table 1)

According to the same procedure as in Example 10, using 3-cyclopentylmethoxy-4-methoxyaniline produced in Example 40(2) instead of 3-(2-indanyloxy)-4-methoxyaniline, the title compound (yield 95.9%) was obtained as a colorless solid.

$^1$H-NMR (400 MHz, CDCl$_3$) δ 1.34–1.39 (2H, m), 1.57–1.66 (4H, m), 1.68 (3H, s), 1.83–1.90 (2H, m), 2.39–2.46 (3H, m), 2.55–2.56 (2H, m), 3.86 (2H, d, J=6.84 Hz), 3.87 (3H, s), 6.38 (1H, broad s), 6.70–6.73 (2H, m), 6.84 (1H, d, J=8.30 Hz).

Example 42

Synthesis of 3-[4-methoxy-3-[2-(1-naphthyl)ethoxy]anilino]-2-cyclopenten-1-one (Compoound No. 42 of Table 1)

(1) Synthesis of 4-methoxy-3-[2-(1-naphthyl)ethoxy]nitrobenzene

According to the same procedure as in Example 9(1), using 2-(1-naphthyl)ethanol instead of 2-indanol, 4-methoxy-3-(2-(1-naphthyl)ethoxy)nitrobenzene (yield 98.6%) was obtained as a yellow solid.

$^1$H-NMR (400 MHz, CDCl$_3$) δ 3.68 (2H, t, J=7.32 Hz), 3.97 (3H, s), 4.41 (2H, t, J=7.32 Hz), 6.90 (1H, d, J=9.28 Hz), 7.42–7.50 (2H, m), 7.50–7.58 (2H, m), 7.71 (1H, d, J=2.93 Hz), 7.79 (1H, dd, J=6.35, 2.93 Hz), 7.88 (1H, dd, J=6.84, 1.47 Hz), 7.90 (1H, dd, J=9.28, 2.93 Hz), 8.11 (1H, d, J=8.30 Hz).

(2) Synthesis of 3-[4-methoxy-3-[2-(1-naphthyl)ethoxy]anilino]-2-cyclopenten-1-one According to the same procedure as in Example 1(2), using 4-methoxy-3-[2-(1-naphthyl)ethoxy]nitrobenzene instead of 3-cyclopentyloxy-4-methoxynitrobenzene, 4-methoxy-3-[2-(1-naphthyl)ethoxy]aniline was obtained as a purple oil. Next, according to the same procedure in Example 1(3), using 4-methoxy-3-[2-(1-naphthyl)ethoxyaniline instead of 3-cyclopentyloxy-4-methoxyaniline, the title compound (yield 95.5%) was obtained as a light yellow solid.

$^1$H-NMR (400 MHz, CDCl$_3$) δ 2.42–2.45 (2H, m), 2.65–2.68 (2H, m), 3.66 (2H, t, J=7.33 Hz), 3.88 (3H, s), 4.30 (2H, t, J=7.33 Hz), 5.40 (1H, s5, 6.34 (1H, broad s), 6.65 (1H, d, J=2.45 Hz), 6.71 (1H, dd, J=8.30, 2.45 Hz), 6.85 (1H, d, J=8.30 Hz), 7.42–7.56 (4H, m), 7.77 (1H, dd, J=6.35, 3.42 Hz), 7.86–7.88 (1H, m), 8.10 (1H, di J=8.30 Hz).

Example 43

Synthesis of 3-[4-methoxy-3-[2-(1-naphthyl)ethoxy]anilino]-2-methyl-2-cyclopenten-1-one (Compound No. 43 of Table 1)

According to the same procedure as in Example 10, using 4-methoxy-3-[2-(1-naphthyl)ethoxy]aniline produced in Example 42(2) instead of 3-(2-indanyloxy)-4-methoxyaniline, the title compound (yield 98.2%) was obtained as a dark brown solid.

$^1$H-NMR (400 MHz, CDCl$_3$) δ 1.63 (3H, s), 2.34–2.36 (2H, m), 2.47–2.48 (2H, m), 3.67 (2H, t, J=7.82 Hz), 3.90 (3H, s), 4.32 (2H, t, J=7.82 Hz), 6.27 (1H, broad s), 6.58 (1H, d, J=2.44 Hz), 6.71 (1H, dd, J=8.30, 2.44 Hz), 6.85 (1H, d, J=8.30 Hz), 7.42–7.45 (2H, m), 7.48–7.55 (2H, m), 7.77 (1H, dd, J=6.84, 2.93 Hz), 7.87–7.89 (1H, m), 8.10 (1H, d, J=7.82 Hz).

Example 44

Synthesis of 3-[3-[(1RS,2RS,4SR)-bicyclo[2.2.1]hept-2-yloxy]4-methoxyanilino]-2-methyl-2-cyclopenten-1-one (Compound No. 44 of Table 1)

According to the same procedure as in Example 10, using 3-[(1RS,2RS,4SR)-bicyclo[2.2.1]hept-2-yloxy]-4-methoxyaniline produced in Example 8(2) instead of 3-(2-indanyloxy)-4-methoxyaniline, the title compound (yield 100%) was obtained as a brown oil.

$^1$H-NMR (400 MHz, CDCl$_3$) δ 1.12–1.18 (2H, m), 1.21–1.23 (1H, m), 1.48–1.54 (1H, m), 1.56–1.64 (2H, m), 1.68 (3H, s), 1.72–1.80 (3H, m), 2.39–2.41 (2H, m), 2.51 (1H, d, J=4.39 Hz), 2.55–2.56 (2H, m), 3.85 (3H, s), 4.16–4.17 (1H, m), 6.47 (1H, broad s), 6.65 (1H, d, J=2.44 Hz), 6.69 (1H, dd, J=8.79, 2.44 Hz), 6.83 (1H, d, J=8.79 Hz).

Example 45

Synthesis of 3-[3-[(1RS,2RS,4SR)-bicyclo[2.2.1]hept-2-yloxy]-4-methoxyanilino]-2-ethyl-2-cyclopenten-1-one (Compound No. 45 of Table 1)

According to the same procedure as in Example 1(3), using 3-[(1RS,2RS,4SR)-bicyclo[2.2.1]hept-2-yloxy]-4-methoxyaniline produced in Example 8(2) instead of 3-cyclopentyloxy-4-methoxyaniline, and using 2-ethyl-1,3-cyclopentanedione instead of 1,3-cyclopentanedione, the title compound (yield 100%) was obtained as a dark brown oil.

$^1$H-NMR (400 MHz, CDCl$_3$) δ 1.05 (3H, t, J=7.81 Hz), 1.14–1.18 (2H, m), 1.21–1.24 (1H, m), 1.49–1.64 (3H, m), 1.71–1.80 (3H, m), 2.22 (2H, q, J=7.81 Hz), 2.36–2.39 (2H, m), 2.50–2.51 (1H, m), 2.53–2.55 (2H, m), 3.85 (3H, s), 4.17 (1H, d, J=6.35 Hz), 6.51 (1H, broad s), 6.65 (1H, d, J=2.44 Hz), 6.69 (1H, dd, J=8.30, 2.44 Hz), 6.83 (1H, d, J=8.30 Hz).

Example 46

Synthesis of 3-[3-[(1RS,2RS,4SR)-bicyclo[2.2.1]hept-2-yloxy]-4-methoxyanilino]-2-methyl-2-cyclohexen-1-one Compound No. 46 of Table 1)

According to the same procedure as in Example 45, using 2-methyl-1,3-cyclohexanedione instead of 2-ethyl-1,3-cyclopentanedione, the title compound (yield 86.0%) was obtained as a pale brown solid.

$^1$H-NMR (400 MHz, CDCl$_3$) δ 1.13–1.26 (3H, m), 1.48–1.63 (3H, m), 1.74–1.80 (3H, m), 1.83 (3H, s), 1.88 (2H, m), 2.36–2.39 (4H, m), 2.50–2.51 (1H, m), 3.85 (3H, s), 4.17 (1H, d, J=5.86 Hz), 6.16 (1H, broad s), 6–59 (1H, d, J=2.44 Hz), 6.64 (1H, dd, J=8.30, 2.44 Hz), 6.82 (1H, d, J=8.30 Hz).

Example 47

Synthesis of 3-[3-[(1RS,2RS,4SR)-bicyclo[2.2.1]hept-2-yloxy]4-methoxy-N-methylanilino]-2-methyl-2-cyclopenten-1-one (Compound No. 47 of Table 1)

According to the same procedure as in Example 26, using 3-[3-[(1RS,2RS,4SR)-bicyclo[2.2.1]hept-2-yloxy]-4-methoxyanilino]-2-methyl-2-cyclopenten-1-one produced in Example 44 instead of 3-(3-cyclopentyloxy-4-methoxyanilino)-2-cyclopenten-1-one, the title compound (yield 42.2%) was obtained as a brown oil.

$^1$H-NMR (400 MHz, CDCl$_3$) δ 1.10–1.16 (2H, m), 1.19–1.22 (1H, m), 1.25 (3H, s), 1.47–1.60 (3H, m), 1.72–1.76 (2H, m), 2.33 (1H, broad), 2.38–2.41 (2H, m), 2.48–2.49 (1H, m), 2.60–2.61 (2H, m), 3.42 (3H, s), 3.85 (3H, s), 4.16 (1H, d, J=6.35 Hz), 6.65 (1H, d, J=2.44 Hz), 6.72 (1H, dd, J=8.79, 2.44 Hz), 6.83 (1H, d, J=8.79 Hz).

Example 48

Synthesis of 3-[3-(2-indanyloxy)-4-methoxyanilino]-2-methyl-2-cyclohexen-1-one (Compound No. 48 of Table 1)

According to the same procedure as in Example 1(3), using 3-(2-indanyloxy)-4-methoxyaniline produced in Example 9(2) instead of 3-cyclopentyloxy-4-methoxyaniline, and using 2-methyl-1,3-cyclohexanedione instead of the 1,3-cyclopentanedione, the title compound (yield 94.2%) was obtained as a light brown solid.

$^1$H-NMR (400 MHz, CDCl$_3$) δ 1.84 (3H, s), 1.89–1.94 (2H, m), 2.36–2.40 (4H, m), 3.24 (2H, dd, J=16.60, 3.42 Hz), 3.39 (2H, dd, J=16.60, 6.35 Hz), 3.83 (3H, s), 5.17 (1H, m), 6.13 (1H, broad s), 6.70–6.72 (2H, m), 6.85 (1H, d, J=8.79 Hz), 7.18–7.23 (2H, m), 7.24–7.28 (2H, m).

Example 49

Synthesis of 3-[4-methoxy-3-[(1-phenylcyclopropyl)methoxy]anilino]-2-cyclopenten-1-one (Compound No. 49 of Table 1)
(1) Synthesis of 4-methoxy-3-[(1-phenylcyclo-propyl)methoxy]nitrobenzene According to the same procedure as in Example 9(1), using 1-phenylcyclopropylmethanol instead of 2-indanol, 4-methoxy-3-[(1-phenylcyclopropyl)methoxy]nitrobenzene (yield 69.3%) was obtained as a yellow solid.

$^1$H-NMR (400 MHz, CDCl$_3$) δ 1.03–1.06 (4H, m), 3.92 (3H, s), 4.14 (2H, s), 6.86 (1H, d, J=8.79 Hz), 7.20–7.24 (1H, m), 7.29–7.32 (2H, m), 7.43–7.45 (2H, m), 7–63 (1H, d, J=2.44 Hz), 7.87 (1H, dd, J38.79, 2.44 Hz)

(2) Synthesis of 3-[4-methoxy-3-[(1-phenylcyclopropyl)methoxy]anilino]-2-cyclopenten-1-one According to the same procedure as in Example 1(2), using 4-methoxy-3-[(1-phenylcyclopropyl)methoxy]nitrobenzene instead of 3-cyclopentyloxy-4-methoxynitrobenzene, 4-methoxy-3-[(1-phenylcyclopropyl)methoxylaniline was obtained as a purple oil. Next, according to the same procedure as in Example 1(3), using 4-methoxy-3-[(1-phenylcyclopropyl)methoxy]aniline instead of 3-cyclopentyloxy-4-methoxyaniline, the title compound (yield 93.3%) was obtained as a light brown solid.

$^1$H-NMR (400 MHz, CDCl$_3$) δ 0.98–1.03 (4H, m), 2.42–2.45 (2H, m), 2.67–2.69 (2H, m), 3.79 (3H, s), 4.03 (2H, s), 5.40 (1H, s), 6.61 (1H, d, J=1.95 Hz), 6.66 (1H, dd, J=8.79, 1.95 Hz), 6.78 (1H, broad s), 6.79 (1H, d, J=8.79 Hz), 7.18–7.22 (1H, m), 7.27–7.31 (2H, m), 7.42–7.44 (2H, m).

Example 50

Synthesis of 3-[4-methoxy-3-[(1-phenylcyclopropyl)methoxy]anilino]-2-methyl-2-cyclopenten-1-one (Compound No. 50 of Table 1)

According to the same procedure as in Example 10, using 4-methoxy-3-[(1-phenylcyclopropyl)methoxy]aniline produced in Example 49(2) instead of 3-(2-indanyloxy)-4-methoxyaniline, the title compound (yield 42.1%) was obtained as a colorless solid.

$^1$H-NMR (400 MHz, CDCl$_3$) δ 0.98–1.00 (2H, m), 1.03–1.06 (2H, m), 1.64 (3H, s), 2.35–2.36 (2H, m), 2.47 (2H, nm), 3.81 (3H, s), 4.07 (2H, s), 6.54 (2H, broad), 6.68 (1H, dd, J=8.79, 1.95 Hz), 6.80 (1H, d, J=8.79 Hz), 7.16–7.31 (3H, m), 7.43–7.44 (2H, m)

Example 51

Synthesis of 3-(3-cyclobutylmethoxy-4-methoxyanilino)-2-cyclopenten-1-one (Compound No. 51 of Table 1)
(1) Synthesis of 3-cyclobutylmethoxy-4-methoxynitrobenzene According to the same procedure as in Example 9(1), using 1-cyclobutylmethanol instead of 2-indanol, 3-cyclobutylmethoxy-4-methoxynitrobenzene (yield 90.6%) was obtained as a yellow solid.

$^1$H-NMR (400 MHz, CDCl$_3$) δ 1.86–2.02 (4H, m), 2.15–2.23 (2H, m), 2.87 (1H, m), 3.96 (3H, s), 4.06 (2H, d, J=6.84 Hz), 6.90 (1H, d, J=9.28 Hz), 7.74 (1H, d, J=2.93 Hz), 7.90 (1H, dd, J=9.28, 2.93 Hz).

(2) Synthesis of 3-(3-cyclobutylmethoxy-4-methoxyanilino)-2-cyclopenten-1-one

According to the same procedure as in Example 1(2), using 3-cyclobutylmethoxy-4-methoxynitrobenzene instead of 3-cyclopentyloxy-4-methoxynitrobenzene, 3-cyclobutylmethoxy-4-methoxyaniline was obtained as a purple oil. Next, according to the same procedure as in Example 1(3), using 3-cyclobutylmethoxy-4-methoxyaniline instead of 3-cyclopentyloxy-4-methoxyaniline, the title compound (yield 92.8%) was obtained as a light brown solid.

¹H-NMR (400 MHz, CDCl₃) δ 1.83–1.98 (4H, m), 2.13–2.20 (2H, m), 2.47–2.49 (2H, m), 2.73–2.74 (2H, m), 2.83 (1H m), 3.86 (3H, s), 3.95 (2H, d, J=7.33 Hz), 5.47 (1H, s), 6.60 (1H, broad s), 6.70 (1H, d, J=8.30 Hz), 6.75 (1H, s), 6.83 (1H, d, J=8.30 Hz).

Example 52

Synthesis of 3-(3-cyclobutylmethoxy-4-methoxyanilino)-2-methyl-2-cyclopenten-1-one (Compound No. 52 of Table 1)

According to the same procedure as in Example 10, using 3-cyclobutylmethoxy-4-methoxyaniline produced in Example 51(2) instead of 3-(2-indanyloxy)-4-methoxyaniline, the title compound (yield 92.7%) was obtained as a colorless solid.

¹H-NMR (400 MHz, CDCl₃) δ 1.68 (3H, s), 1.84–2.00 (4H, m), 2.07–2.21 (2H, m), 2.39–2.41 (2H, m), 2.56–2.57 (2H, m), 2.84 (1H, m, J=6.84 Hz), 3.87 (3H, s), 3.97 (2H, d, J=6.84 Hz), 6.44 (1H, broad s), 6.71–6.73 (2H, m), 6.84 (1H, d, J=8.30 Hz).

Example 53

Synthesis of 3-[3-[2-(2-indanyl)ethoxy]-4-methoxyanilino]-2-methyl-2-cyclohexen-1-one (Compound No. 53 of Table 1)

According to the same procedure as in Example 46, using 3-(2-(2-indanyl)ethoxy]-4-methoxyaniline produced in Example 34(2) instead of 3-[(1RS,2RS,4SR)-bicyclo[2.2.1]hept-2-yloxy]-4-methoxyaniline, the title compound (yield 92.0%) was obtained as a light brown solid.

¹H-NMR (400 MHz, CDCl₃) δ 1.84 (3H, s), 1.89 (2H, m), 2.09 (2H, q, J=6.35 Hz), 2.36–2.39 (4H, m), 2.68–2.70 (3H, m), 3.12–3.14 (2H, m), 3.88 (3H, s), 4.09 (2H, t, J=6.35 Hz), 6.13 (1H, broad s), 6.67 (1H, s), 6.68 (1H, d, J=8.30 Hz), 6.84 (1H, d, J=8.30 Hz), 7.14 (2H, m), 7.19–7.20 (2H, m).

Example 54

Synthesis of 3-(3-cyclopentylmethoxy-4-methoxyanilino)-2-methyl-2-cyclohexen-1-one (Compound No. 54 of Table 1)

According to the same procedure as in Example 46, using 3-cyclopentylmethoxy-4-methoxyaniline produced in Example 40(2) instead of 3-[(1RS,2RS,4SR)-bicyclo[2.2.1]hept-2-yloxy]-4-methoxyaniline, the title compound (yield 91.6%) was obtained as a light brown solid.

¹H-NMR (400 MHz, CDCl₃) δ 1.35–1.39 (2H, m), 1.60–1.66 (4H, m), 1.83 (3H, s), 1.83–1.90 (4H, m), 2.36–2.39 (4H, m), 2.44 (1H, m), 3.86 (2H, d, J=9.76 Hz), 3.87 (3H, s), 6.15 (1H, broad s), 6.65–6.67 (2H, m), 6.83 (1H, d, J=8.79 Hz).

Example 55

Synthesis of 3-(3-cyclohexyloxy-4-methoxyanilino)-2-methyl-2-cyclohexen-1-one (Compound No. 55 of Table 1)

According to the same procedure as in Example 46, using 3-cyclohexyloxy-4-methoxyaniline produced in Example 13(2) instead of 3-[(1RS,2RS,4SR)-bicyclo[2.2.1]hept-2-yloxy]-4-methoxyaniline, the title compound (yield 81.2%) was obtained as a light brown solid.

¹H-NMR (400 MHz, CDCl₃) δ 1.24–1.42 (3H, m), 1.49–1.62 (2H, m), 1.65–1.92 (5H, m), 1.83 (3H, s), 2.01–2.04 (2H, m), 2.37–2.39 (4H, m), 3.86 (3H, s), 4.18 (1H, m), 6.11 (1H, broad s), 6.66–6.68 (2H, m), 6.84 (1H, d, J=9.27 Hz).

Example 56

Synthesis of 3-(N-benzyl-3-cyclohexyloxy-4-methoxyanilino)-2-cyclopenten-1-one (Compound No. 56 of Table 1)

According to the same procedure as in Example 26, using 3-(3-cyclohexyloxy-4-methoxyanilino)-2-cyclopenten-1-one produced in Example 13(3) instead of 3-(3-cyclopentyloxy-4-methoxyanilino)-2-cyclopenten-1-one, and using benzyl bromide instead of methyl iodide, the title compound (yield 89.4%) was obtained as a yellow oil.

¹H-NMR (400 MHz, CDCl₃) δ 1.22–1.29 (3H, m), 1.41–1.49 (2H, m), 1.56–1.58 (1H, m), 1.76–1.79 (2H, m), 1.85–1.88 (2H, m), 2.41 (4H, broad s), 3.84 (3H, s), 3.96–4.01 (1H, m), 4.75 (2H, s), 5.38 (1H, broad s), 6.52 (1H, d, J=2.44 Hz), 6.69 (1H, dd, J=8.79, 2.44 Hz), 6.81 (1H, d, J=8.79 Hz), 7.20–7.34 (5H, m).

Example 57

Synthesis of 3-[3-cyclohexyloxy-4-methoxy-N-(2-naphthylmethyl)anilino]-2-cyclopenten-1-one (Compound No. 57 of Table 1)

According to the same procedure as in Example 56, using 2-(bromomethyl)naphthalene instead of benzyl bromide, the title compound (yield 85.1%) was obtained as a light brown oil.

¹H-NMR (400 MHz, CDCl₃) δ 1.08–1.18 (3H, m), 1.31–1.40 (2H, m), 1.47–1.51 (1H, m), 1.61–1.64 (2H, m), 1.73–1.75 (2H, m), 2.42 (4H, broad s), 3.82 (3H, s), 3.84–3.90 (1H, m), 4.90 (2H, s), 5.47 (1H, broad s), 6.49 (1H, broad), 6.72 (1H, dd, J=8.79, 2.44 Hz), 6.80 (1H, d, J=8.79 Hz), 7.35 (1H, d, J=8.30 Hz), 7.46–7.48 (2H, m), 7.60 (1H, s), 7.74–7.83 (3H, m).

Example 58

Synthesis of 3-[3-cyclopentyloxy-4-methoxy-N-(2-quinolylemethyl)anilino]-2-cyclopenten-1-one (Compound No. 58 of Table 1)

According to the same procedure as in Example 26, using 2-(chloromethyl)quinoline hydrochloride instead of methyl iodide, the title compound (yield 96.8%) was obtained as a black-brown oil.

¹H-NMR (400 MHz, CDCl₃) δ 1.52 (2H, m), 1.76 (6H, m), 2.42 (2H, broad), 2.61 (2H, broad), 3.83 (3H, s), 4.60 (1H, m), 5.08 (2H, s), 5.19 (1H, broad), 6.79–6.85 (3H, m), 7.38 (1H, d, J=8.30 Hz), 7.55 (1H, dd, J=7.33, 6.83 Hz), 7.73 (1H, dd, J=8.30, 6.83 Hz), 7.82 (1H, d, J=8.30 Hz), 8.03 (1H, d, J=8.30 Hz), 8.15 (1H, d, J=8.30 Hz).

Example 59

Synthesis of 3-(3-cyclopentyloxy-4-methoxy-N-propylanilino)-2-cyclopenten-1-one (Compound No. 59 of Table 1)

According to the same procedure as in Example 26, using propyl iodide instead of methyl iodide, the title compound (yield 95.1%) was obtained as a brown oil.

¹H-NMR (400 MHz, CDCl₃) δ 0.99 (3H, t, J=7.33 Hz), 1.63 (4H, m), 1.82–1.95 (6H, m), 2.35 (4H, broad), 3.50

(2H, t, J=7.32 Hz), 4.74 (1H, M), 5.20 (1H, broad), 6.66 (1H, d, J=2.45 Hz), 6.71 (1H, dd, J=8.30, 2.45 Hz), 6.86 (1H, d, J=8.30 Hz).

Example 60

Synthesis of 3-(N-cyclopentyl-3-cyclopentyloxy-4-methoxyanilino)-2-cyclopenten-1-one (Compound No. 60 of Table 1)

According to the same procedure as in Example 26, using bromocyclopentane instead of methyl iodide, the title compound (yield 27.3%) was obtained as a light brown oil.

$^1$H-NMR (400 MHz, CDCl$_3$) δ 1.46 (2H, broad), 1.55 (4H, m), 1.63 (2H, m), 1.85–1.93 (8H, m), 2.30 (4H, broad), 3.87 (3H, s), 4.11 (1H, broad), 4.73 (1H, m), 5.26 (1H broad), 6.59 (1H, d, J=2.44 Hz), 6.64 (1H, dd, J=8.30, 2.44 Hz), 6.84 (1H, d, J=8.30 Hz).

Example 61

Synthesis of 3-[3-cyclopentyloxy-4-methoxy-N-(2-pyridylmethyl)anilino]-2-cyclopenten-1-one (Compound No. 61 of Table 1)

According to the same procedure as in Example 26, using 2-(chloromethyl)pyridine hydrochloride instead of methyl iodide, the title compound (yield 81.6%) was obtained as a yellow-brown oil.

$^1$H-NMR (400 MHz, CDCl$_3$) δ 1.60–1.63 (2H, m), 1.80–1.87 (6H, m), 2.41–2.58 (4H, broad), 3.84 (3H, s), 4.65 (1H, broad), 4.90 (2H, s), 5.12 (1H, broad), 6.76–6.82 (3H, m), 7.19–7.22 (2H, m), 7.66 (1H, ddd, J=7.81, 7.81, 1.47 Hz), 8.58 (1H, d, J=4.40 Hz).

Example 62

Synthesis of 3-[3-cyclopentyloxy-4-methoxy-N-(2-naphthylmethyl)anilino]-2-cyclopenten-1-one (Compound No. 62 of Table 1)

According to the same procedure as in Example 26, using 2-(bromomethyl)naphthalene instead of methyl iodide, the title compound (yield 92.3%) was obtained as a light pink oil.

$^1$H-NMR (400 MHz, CDCl$_3$) δ 1.46–1.49 (2H, m), 1.65–1.71 (6H, m), 2–42 (4H, broad), 3.82 (3H, s), 4.48 (1H m), 4.91 (2H, s), 5.45 (1H, broad), 6.49 (1H, broad), 6.69 (1H, dd, J=8.79, 2.44 Hz), 6.78 (1H, d, J=8.79 Hz), 7.35 (1H, dd, J=8.30, 1.47 Hz), 7.47–7.49 (2H, m), 7.61 (1H, s), 7.75–7.77 (1H, m), 7.80–7.83 (2H, m).

Example 63

Synthesis of 3-[3-cyclopentyloxy-4-methoxy-N-(3-pyridylmethyl)anilino]2-cyclopenten-1-one (Compound No. 63 of Table 1)

According to the same procedure as in Example 26, using 3-(chloromethyl)pyridine hydrochloride instead of methyl iodide, the title compound (yield 77.2%) was obtained as a brown oil.

$^1$H-NMR (400 MHz, CDCl$_3$) δ 1.59–1.60 (2H, m), 1.80–1.85 (6H, m), 2.41 (4H, broad), 3.84 (3H, s)1 4.61 (1H, m), 4.78 (2H, s), 5.29 (1H, broad), 6.52 (1H, d, J=2.44 Hz), 6.64 (1H, dd, J=8.30, 2.44 Hz), 6.80 (1H, d, J=8.30 Hz), 7.25–7.28 (1H, m), 7.56 (1H, d, J=7.32 Hz), 8.45 (1H, d, J=1.95 Hz), 8.55 (1H, dd, J=4.88, 1.95 Hz).

Example 64

Synthesis of 3-(3-cyclopentyloxy-4-methoxy-N-pentylanilino)-2-cyclopenten-1-one (Compound No. 64 of Table 1)

According to the same procedure as in Example 26, using amyl iodide instead of methyl iodide, the title compound (yield 100%) was obtained as a brown oil.

$^1$H-NMR (400 MHz, CDCl$_3$) δ 0.88 (3H, t, J=6.84 Hz), 1.25–1.33 (4H, m), 1.63–1.68 (4H, m), 1.82–1.86 (2H, m), 1.89–1.95 (4H, m), 2.35 (4H, broad), 3.53 (2H, bt, J=7.81 Hz), 3.87 (3H, s), 4.74 (1H, m), 5.20 (1H, broad), 6.65 (1H, d, J=2.44 Hz), 6.70 (1H, dd, J=8.30, 2.44 Hz), 6.86 (1H, d, J=8.30 Hz).

Example 65

Synthesis of 3-[3-(2-indanyloxy)-4-methoxy-N-methylanilino]-2-cyclohexen-1-one (Compound No. 65 of Table 1)

According to the same procedure as in Example 26, using 3-[3-(2-indanyloxy)-4-methoxyanilino]-2-cyclohexen-1-one produced in Example 19(2) instead of 3-(3-cyclopentyloxy-4-methoxyanilino)-2-cyclopenten-1-one, the title compound (yield 83.2%) was obtained as a yellow oil.

$^1$H-NMR (400 MHz, CDCl$_3$) δ 1.90–1.93 (2H, m), 2.24 (2H, t, J=6.35 Hz), 2.32 (2H, t, J=6.35 Hz), 3.23 (2H, dd, J=16.60, 3.42 Hz), 3.23 (3H, s), 3.39 (2H, dd, J=16.60, 6.34 Hz), 3.83 (3H, s), 5.16 (1H, m, J=3.42 Hz), 5.31 (1H, s), 6.69 (1H, d, J=2.44 Hz), 6.72 (1H, dd, J=8.30, 2.44 Hz), 6.86 (1H, d, J=8.30 Hz), 7.18–7.21 (2H, m), 7.24–7.26 (2H, m).

Example 66

Synthesis of 3-[N-benzyl-3-(2-indanyloxy)-4-methoxyanilino]-2-cyclohexen-1-one (Compound No. 66 of Table 1)

According to the same procedure as in Example 65, using benzyl bromide instead of methyl iodide, the title compound (yield 55.6%) was obtained as a light brown oil $^1$H-NMR (400 MHz, CDCl$_3$) δ 1.94–1.97 (2H, m), 2.31–2.36 (4H, m), 3.09 (2H, dd, J=16.60, 3.91 Hz), 3.23 (2H, dd, J=16.60, 6.34 Hz), 3.80 (3H, s), 4.79 (2H, s), 5.00 (1H, m, J=3.42 Hz), 5.45 (1H, s), 6.56 (1H, d, J=2.44 Hz), 6.72 (1H, dd, J=8.30, 2.44 Hz), 6.82 (1H, d, J=8.30 Hz), 7.16–7.23(7H, m), 7.28–7.35 (2H, m).

Example 67

Synthesis of 3-[3-(2-indanyloxy)-4-methoxy-N-(2-naphthylmethyl)anilino]-2-cyclohexen-1-one (Compound No. 67 of Table 1)

According to the same procedure as in Example 65, using 2-(bromomethyl)naphthalene instead of methyl iodide, the title compound (yield 48.9%) was obtained as a light brown oil.

$^1$H-NMR (400 MHz, CDCl$_3$) δ 1.96–1.99 (2H, m), 2.33–2.38 (4H, m), 2.95 (2H, m), 3.06 (26, dd, J=16.60, 6.35 Hz), 3.79 (3H, s), 4.90 (1H, m, J=3.42 Hz), 4.94 (2H, s), 5.56 (1H, s), 6.50 (1H, d, J=2.44 Hz), 6.76 (1H, dd, J=8.79, 2.44 Hz), 6.82 (1H, d, J=8.79 Hz), 7.04–7.06 (2H, m), 7.12–7.14 (26, m), 7.35–7.37 (1H, m), 7.47–7.50 (2H, m), 7.62 (1H, s), 7.77–7.84 (3H, m).

Example 68

Synthesis of 3-[3-(2-indanyloxy)-4-methoxy-N-(2-pyridylmethyl)anilino]-2-cyclohexen-1-one (Compound No. 68 of Table 1)

According to the same procedure as in Example 65, using 2-(chloromethyl)pyridine hydrochloride instead of methyl iodide, the title compound (yield 70.5%) was obtained as a light brown oil.

¹H-NMR (400 MHz, CDCl₃) δ 1.94–1.99 (2H, m), 2.31 (2H, t, J=6.35 Hz), 2.40 (2H, t, J=6.35 Hz), 3.16 (2H, dd, J=16.60, 3.42 Hz), 3.32 (2H, dd, J=16.60, 6.84 Hz), 3.81 (3H, s), 4.92 (2H, s), 5.09 (1H, m), 5.29 (1H, s), 6.82–6.85 (3H, m), 7.17–7.28 (6H, m), 7.67 (1H, ddd, J=7.81, 7.81, 1.96 Hz), 8.58 (1H, bd, J=3.91 Hz).

Example 69

Synthesis of 2-benzyl-3-(3-cyclopentyloxy-4-methoxyanilino)-2-cyclohexen-1-one (Compound No. 69 of Table 1)

According to the same procedure as in Example 1, using 2-benzyl-1,3-cyclohexanedione instead of 1,3-cyclopentanedione, the title compound (yield 94.1%) was obtained as a light pink solid.

¹H-NMR (400 MHz, CDCl₃) δ 1.61 (2H, broad), 1.82–1.91 (6H, m), 1.95 (2H, m, J=6.35 Hz), 2.40 (2H, t, J=6.35 Hz), 2.47 (2H, t, J=6.35 Hz), 3.81 (3H, s), 3.84 (2H, s), 4.63 (1H, m), 6.21 (1H, broad s), 6.31 (1H, d, J=2.44 Hz), 6.40 (1H, dd, J=8.79, 2.44 Hz), 6.73 (1H, d, J=8.79 Hz), 7.18–7.31 (5H, m).

Example 70

Synthesis of 3-(3-cyclopentyloxy-4-methoxy-N-methylanilino)-2-methyl-2-cyclopenten-1-one (Compound No. 70 of Table 1)

According to the same procedure as in Example 26, using 3-(3-cyclopentyloxy-4-methoxyanilino)-2-methyl-2-cyclopenten-1-one produced in Example 4 instead of 3-(3-cyclopentyloxy-4-methoxyanilino)-2-cyclopenten-1-one, the title compound (yield 62.8%) was obtained as a brown solid.

¹H-NMR (400 MHz, CDCl₃) δ 1.26 (3H, s), 1.59–1.62 (2H, m), 1.81–1.94 (6H, m), 2.39–2.41 (2H, m), 2.59–2.60 (2H, m), 3.42 (3H, s), 3.86 (3H, s), 4.73 (1H, m, J=3.42 Hz), 6.69 (1H, d, J=2.44 Hz), 6.73 (1H, dd, J=8.79, 2.44 Hz), 6.83 (1H, d, J=8.79 Hz).

Example 71

Synthesis of 3-(N-benzyl-3-cyclopentyloxy-4-methoxyanilino)-2-methyl-2-cyclopenten-1-one (Compound No. 71 of Table 1)

According to the same procedure as in Example 70, using benzyl bromide instead of methyl iodide, the title compound (yield 27.5%) was obtained as a brown solid.

¹H-NMR (400 MHz, CDCl₃) δ 1.30 (3H, s), 1.55–1.56 (2H, m), 1.77 (6H, broad), 2.41–2.43 (2H, m), 2.66–2.67 (2H, m), 3.79 (3H, s), 4.55 (1H, m), 4.92 (2H, s), 6.55 (1H, d, J=2.44 Hz), 6.66 (1H, dd, J=8.79, 2.44 Hz), 6.75 (1H, d, J=8.79 Hz), 7.21–7.37 (5H, m).

Example 72

Synthesis of 3-[3-cyclopentyloxy-4-methoxy-N-(2-quinolylemethyl)anilino]-2-methyl-2-cyclopenten-1-one (Compound No. 72 of Table 1)

According to the same procedure as in Example 70, using 2-(chloromethyl)quinoline hydrochloride instead of methyl iodide, the title compound (yield 36.2%) was obtained as a red-brown oil.

¹H-NMR (400 MHz, CDCl₃) δ 1.29 (3H, s), 1.50 (2H, broad), 1.73 (6H, broad), 2.42–2.43 (2H, m), 2.76 (2H, broad), 3.81 (3H, s), 4.55 (1H, m), 5.20 (2H, s), 6.74–6.80 (3H, m), 7.35 (1H, d, J=8.30 Hz), 7.55 (1H, m), 7.74 (1H, m), 7.83 (1H, d, J=8.30 Hz), 8.04 (1H, d, J=8.30 Hz), 8.16 (1H, d, J=8.30 Hz).

Example 73

Synthesis of 3-[3-(2-indanyloxy)-4-methoxy-N-(4-pyridylmethyl)anilino]-2-methyl-2-cyclopenten-1-one (Compound No. 73 of table 1)

According to the same procedure as in Example 28, using 3-[3-(2-indanyloxy)-4-methoxyanilino]-2-methyl-2-cyclopenten-1-one produced in Example 10 instead of 3-(3-cyclopentyloxy-4-methoxyanilino)-2-cyclopenten-1-one, and using 4-(chloromethyl)pyridine hydrochloride instead of methyl iodide, the title compound (yield 38.8%) was obtained as a brown oil.

¹H-NMR (400 MHz, CDCl₃) δ 1.34 (3H, s), 2.43–2.45 (2H, m), 2.63 (2H, m), 3.12 (2H, dd, J=16.60, 3.90 Hz), 3.25 (2H, dd, J=16.60, 6.84 Hz), 3.80 (3H, s), 4.95 (2H, s), 5.04 (1H, m, J=3.42 Hz), 6.64 (1H, d, J=2.44 Hz), 6.72 (1H, dd, J=8.30, 2.44 Hz), 6.79 (1H, d, J=8.30 Hz), 7.17–7.23 (6H, m), 8.62–8.64 (2H, m).

Example 74

Synthesis of 3-[3-(2-indanyloxy)-4-methoxy-N-(2-naphthylmethyl)anilino]-2-methyl-2-cyclopenten-1-one (Compound No. 74 of Table 1)

According to the same procedure as in Example 73, using 2-(bromomethyl) naphthalene instead of 4-(chloromethyl) pyridine hydrochloride, the title compound (yield 24.9%) was obtained as a brown oil.

¹H-NMR (400 MHz, CDCl₃) δ 1.35 (3H, s), 2.45–2.48 (2H, m), 2.75 (2H, broad), 2.93 (2H, dd, J=16.60, 3.91 Hz), 3.04 (2H, dd, J=16.60, 6.35 Hz), 3.78 (3H, s), 4.86 (1H, m, J=3.42 Hz), 5.09 (2H, s), 6.54 (1H, broad s), 6.77 (2H, s), 7.03–7.05 (2H, m), 7.11–7.13 (2H, m), 7.36–7.39 (1H, m), 7.50–7.52 (2H, m), 7.64 (1H, s), 7.80–7.88 (3H, m).

Example 75

Synthesis of 3-(3-cyclopentyloxy-4-methoxyanilino)-2-methyl-2-cyclohexen-1-one (Compound No. 75 of Table 1)

According to the same procedure as in Example 46, using 3-cyclopentyloxy-4-methoxyaniline produced in Example 1(2) instead of 3-[(1RS,2RS,4SR)-bicyclo[2.2.1]hept-2-yloxy]-4-methoxyaniline, the title compound (yield 85.9%) was obtained as a light gray solid.

¹H-NMR (400 MHz, CDCl₃) δ 1.63 (2H, m), 1.83 (3H, s), 1.87–1.96 (8H, m), 2.38 (4H, t, J=6.35 Hz), 3.86 (3H, s), 4.75 (1H, m, J=2.93 Hz), 6.13 (1H, broad s), 6.64–6.66 (2H, m), 6.82 (1H, d, J=7.82 Hz).

Example 76

Synthesis of 3-[2-indanyloxy)-4-methoxy-N-methylanilino]-2-cyclopenten-1-one (Compound No. 76 of Table 1)

According to the same procedure as in Example 26, using 3-[3-(2-indanyloxy)-4-methoxyanilino]-2-cyclopenten-1-one produced in Example 9(3) instead of 3-(3-cyclopentyloxy-4-methoxyanilino)-2-cyclopenten-1-one, the title compound (yield 100%) was obtained as a light brown oil.

¹H-NMR (400 MHz, CDCl₃) δ 2.42 (4H, broad), 3.23 (2H, dd, J=16.60, 3.42 Hz), 3.32 (3H, s), 3.39 (2H, dd, J=16.60, 6.83 Hz), 3.84 (3H, s), 5.16 (2H, m), 6.76–6.80 (2H, m), 6.88 (1H, d, J=8.30 Hz), 7.18–7.26 (4H, m).

Example 77

Synthesis of 3-[N-benzyl-3-(2-indanyloxy)-4-methoxyanilino]-2-cyclopenten-1-one (Compound No. 77 of Table 1)

According to the same procedure as in Example 76, using benzyl bromide instead of methyl iodide, the title compound (yield 94.3%) was obtained as a colorless oil.

$^1$H-NMR (400 MHz, CDCl$_3$) δ 2.43 (4H, broad), 3.08 (2H, dd, J=16.60, 3.42 Hz), 3.22 (2H, dd, J=16.60, 6.84 Hz), 3.81 (3H, s), 4.78 (2H, s), 4.98 (1H, m), 5.32 (1H, broad), 6.55 (1H, broad s), 6.74 (1H, dd, J=8.79, 2.45 Hz), 6.82 (1H, d, J=8.79 Hz), 7.16–7.36 (9H, m).

Example 78

Synthesis of 3-[3-(2-indanyloxy)-4-methoxy-N-(4-pyridylmethyl)anilino]-2-cyclopenten-1-one (Compound No. 78 of Table 1)

According to the same procedure as in Example 76, using 4-(chloromethyl)pyridine hydrochloride instead of methyl iodide, the title compound (yield 77.2%) was obtained as a brown oil.

$^1$H-NMR (400 MHz, CDCl$_3$) δ 2.45–2.55 (4H, broad), 3.13 (2H, dd, J=16.60, 3.42 Hz), 3.28 (2H, dd, J=16.60, 6.84 Hz), 3.82 (3H, s), 4.79 (2H, s), 5.06 (1H, m), 5.20 (1H, broad), 6.65 (1H, d, J=2.44 Hz), 6.76 (1H dd, J=8.30, 2.44 Hz), 6.84 (1H, d, J=8.30 Hz), 7.18–7.24 (6H, m), 8.60–8.62 (2H, m).

Example 79

Synthesis of 3-[3-(2-indanyloxy)-4-methoxy-N-(2-naphthylmethyl)anilino]-2-cyclopenten-1-one (Compound No. 79 of Table 1)

According to the same procedure as in Example 76, using 2-(bromomethyl)naphthalene instead of methyl iodide, the title compound (yield 100%) was obtained as a light brown solid.

$^1$H-NMR (400 MHz, CDCl$_3$) δ 2.45 (4H, broad), 2.92 (2H, dd, J=16.60, 3.42 Hz), 3.03 (2H, dd, J=16.60, 6.83 Hz), 3.79 (3H, s), 4.86 (1H, m, J=3.42 Hz), 4.93 (2H, s), 5.51 (1H, broad), 6.48 (1H, broad), 6.77 (1H, dd, J=8.79, 2.44 Hz), 6.82 (1H, d, J=8.79 Hz), 7.03–7.05 (2H, m), 7.11–7.14 (2H, m), 7.38 (1H, m), 7.50–7.52 (2H, m), 7.62 (1H, s), 7.78–7.80 (1H, m), 7.83–7.85 (2H, m).

Example 80

Synthesis of 3-[3-(2-indanyloxy)-4-methoxy-N-(2-quinolylmethyl)anilino]-2-cyclopenten-1-one (Compound No. 80 of Table 1)

According to the same procedure as in Example 76, using 2-(chloromethyl)quinoline hydrochloride instead of methyl iodide, the title compound (yield 76.1%) was obtained as a light brown solid.

$^1$H-NMR (400 MHz, CDCl$_3$) δ 2.45–2.64 (4H, broad), 3.06 (2H, dd, J=16.60, 3.42 Hz), 3.20 (2H, dd, J=16.60, 6.35 Hz), 3.80 (3H, s), 5.01 (1H, m), 5.09 (2H, s), 5.22 (1H, broad), 6.82–6.90 (3H, m), 7.11–7.17 (4H, m), 7.41 (1H, broad), 7.56 (1H, dd, J=8.30, 6.83 Hz), 7.72 (1H, dd, J=8.30, 6.83 Hz), 7.83 (1H, d, J=8.30 Hz), 8.04 (1H, d, J=8.30 Hz), 8.17 (1H, d, J=8.79 Hz).

Example 81

Synthesis of 3-[N-benzyl-3-[(1RS,2RS,4SR)-bicyclo[2.2.1]hept-2-yloxy]4-methoxyanilino]-2-cyclopenten-1-one (Compound No. 81 of Table 1)

According to the same procedure as in Example 26, using 3-[3-[(1RS,2RS,4SR)-bicyclo[2.2.1]hept-2-yloxy]-4-methoxyanilino]2-cyclopenten-1-one produced in Example 8(3) instead of 3-(3-cyclopentyloxy-4-methoxyanilino)-2-cyclopenten-1-one, and using benzyl bromide instead of methyl iodide, the title compound (yield 92.3%) was obtained as a light yellow oil.

$^1$H-NMR (400 MHz, CDCl$_3$) δ 1.00–1.11 (2H, m), 1.16–1.18 (1H, m), 1.47–1.69 (5H, m), 2.29 (1H, m), 2.34 (1H, m), 2.40 (4H, broad), 3.83 (3H, s), 3.96–3.98 (1H, m), 4.76 (2H, s), 5.30 (1H, broad), 6.46 (1H, broad), 6.67 (1H, dd, J=8.30, 2.44 Hz), 6.79 (1H, d, J=8.30 Hz), 7.20–7.22 (2H, m), 7.28–7.34 (3H, m).

Example 82

Synthesis of 3-[3-[(1RS,2RS,4SR)-bicyclo[2.2.1]hept-2-yloxy]4-methoxy-N-(2-quinolinemethyl)anilino]-2-cyclopenten-1-one (Compound No. 82 of Table 1)

According to the same procedure as in Example 81, using 2-(chloromethyl)quinoline hydrochloride instead of benzyl bromide, the title compound (yield 92.8%) was obtained as a brown oil.

$^1$H-NMR (400 MHz, CDCl$_3$) δ 0.96–1.02 (2H, m), 1.11–1.14 (1H, m), 1.43–1.44 (3H, m), 1.54 (1H, m), 1.62–1–65 (1H, m), 2.23 (1H, broad), 2.33 (1H, broad), 2.43–2.67 (4H, broad), 3.82 (3H, s), 3.97 (1H, broad), 5.07 (2H, s), 5.22 (1H, broad), 6.72 (1H, broad), 6.79–6.84 (2H, m), 7.38–7.39 (1H, m), 7.55 (1H, m), 7.73 (1H, m), 7.82 (1H, d, J=8.30 Hz), 8.03 (1H, d, J=8.30 Hz), 8.15 (1H, d, J=8.30 Hz).

Example 83

Synthesis of 3-[3-[rel(1R,2R,4S)-bicyclo[2.2.1]hept-2-yloxy]-4-methoxyanilino]-2-cyclohexen-1-one (Compound No. 83 of Table 1)

According to the same procedure as in Example 8, using 1,3-cyclohexanedione instead of 1,3-cyclopentanedione, the title compound (yield 90.1%) was obtained as a light yellow solid.

$^1$H-NMR (400 MHz. CDCl$_3$) δ 1.11–1.13 (2H, m), 1.19–1.21 (1H, m), 1.48–1.58 (3H, m), 1.72–1.75 (2H, m), 2.04 (2H, m, J=6.35 Hz), 2.32–2.37 (1H, m), 2.36 (2H, t, J=6.35 Hz), 2.46–2.49 (1H, m), 2.48 (2H, t, J=6.35 Hz), 3.83 (3H, s), 4.13–4.14 (1H, m), 5.42 (1H, s), 5.96 (1H, broad s), 6.63 (1H, d, J=2.44 Hz), 6.69 (1H, dd, J=8.30, 2.44 Hz), 6.80 (1H, d, J=8.30 Hz).

Example 84

Synthesis of 3-[N-benzyl-3-[rel(1R,2R,4S)-bicyclo[2.2.1]hept-2-yloxy]-4-methoxyanilino]-2-cyclohexen-1-one (Compound No. 84 of Table 1)

According to the same procedure as in Example 26, using 3-[3-[rel(1R,2R,4S)-bicyclo[2.2.1]hept-2-yloxy]-4-methoxyanilino]-2-cyclohexen-1-one produced in Example 83 instead of 3-(3-cyclopentyloxy-4-methoxyanilino)-2-cyclopenten-1-one, and using benzyl bromide instead of methyl iodide, the title compound (yield 60.8%) was obtained as a light yellow oil.

$^1$-NMR (400 MHz, CDCl$_3$) δ 1.04–1.10 (2H, m), 1.16–1.18 (1H, m), 1.48–1.54 (3H, m), 1.60–1.61 (1H, m), 1.67–1.69 (1H, m), 1.93 (2H, m, J=6.35 Hz), 2.30–2.31 (4H, broad), 2.33 (1H, m), 2.35 (1H, m), 3.83 (3H, s), 3.99–4.01 (1H, m), 4.77 (2H, s), 5.44 (1H, s), 6.47 (1H, d, J=2.44 Hz), 6.65 (1H, dd, J=8.30, 2.44 Hz), 6.79 (1H, d, J=8.30 Hz), 7.19–7.21 (2H, m), 7.25–7.32 (3H, m).

Example 85

Synthesis of 3-[3-[(1RS,2RS,4SR)-bicyclo[2.2.1]hept-2-yloxy]4-methoxy-N-(4-pyridylmethyl)anilino]-2-cyclohexen-1-one (Compound No. 85 of Table 1)

According to the same procedure as in Example 84, using 4-(chloromethyl)pyridine hydrochloride instead of benzyl bromide, the title compound (yield 44.6%) was obtained as a light brown oil.

$^1$H-NMR (400 MHz, CDCl$_3$) δ 1.07–1.13 (2H, m), 1.18–1.21 (1H, m), 1.57–1.70 (5H, m), 1.94 (2H, m, J=6.35 Hz), 2.29–2.33 (5H, m), 2.38 (1H, m), 3.84 (3H, s), 4.05–4.06 (1H, m), 4.77 (2H, s), 5.32 (1H, s), 6.52 (1H, d, J=2.44 Hz), 6.67 (1H, dd, J=8.30, 2.44 Hz), 6.80 (1H, d, J=8.30 Hz), 7.17 (2H, d, J=5.86 Hz), 8.57 (2H, d, J=5.86 Hz).

TABLE 1

| Compound No. | R$_1$ | R$_2$ | R$_3$ | R$_4$ | R$_5$ | R$_6$ | R$_7$ | R$_8$ | X |
|---|---|---|---|---|---|---|---|---|---|
| 1 | cyclopentyl | Me | H | H | H | H | H | H | — |
| 2 | cyclopentyl | Me | H | H | H | H | H | H | CH$_2$ |
| 3 | cyclopentyl | Me | H | H | H | H | Me | Me | CH$_2$ |
| 4 | cyclopentyl | Me | H | Me | H | H | H | H | — |
| 5 | cyclopentyl | Me | H | H | H | H | Me | H | CH$_2$ |
| 6 | cyclopentyl | Me | H | Cl | H | H | H | H | — |
| 7 | cyclopentyl | Me | H | Br | H | H | H | H | — |
| 8 | norbornyl | Me | H | H | H | H | H | H | — |
| 9 | indanyl | Me | H | H | H | H | H | H | — |
| 10 | indanyl | Me | H | Me | H | H | H | H | — |

TABLE 1-continued

| Compound No. | R₁ | R₂ | R₃ | R₄ | R₅ | R₆ | R₇ | R₈ | X |
|---|---|---|---|---|---|---|---|---|---|
| 11 | phenylpropyl | Me | H | H | H | H | H | H | — |
| 12 | phenylpropyl | Me | H | Me | H | H | H | H | — |
| 13 | cyclohexylmethyl | Me | H | H | H | H | H | H | — |
| 14 | cyclohexylmethyl | Me | H | Me | H | H | H | H | — |
| 15 | cyclopropylethyl | Me | H | H | H | H | H | H | — |
| 16 | cyclopropylethyl | Me | H | Me | H | H | H | H | — |
| 17 | CH₃(CH₂)₃ | Me | H | H | H | H | H | H | — |
| 18 | CH₃(CH₂)₃ | Me | H | Me | H | H | H | H | — |
| 19 | 2-indanylmethyl | Me | H | H | H | H | H | H | CH₂ |
| 20 | benzyl (phenylethyl) | Me | H | H | H | H | H | H | CH₂ |
| 21 | cyclopentylmethyl | Me | H | H | H | H | H | H | NH |
| 22 | cyclopentylmethyl | Me | H | H | H | H | H | H | NBn |
| 23 | norbornylmethyl | Me | H | H | H | H | H | H | NH |

TABLE 1-continued
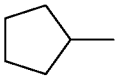
| Compound No. | R₁ | R₂ | R₃ | R₄ | R₅ | R₆ | R₇ | R₈ | X |
|---|---|---|---|---|---|---|---|---|---|
| 24 | 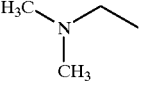 | Me | H | 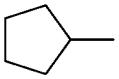 | H | H | H | H | — |
| 25 | 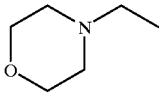 | Me | H |  | H | H | H | H | — |
| 26 | 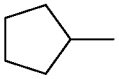 | Me | Me | H | H | H | H | H | — |
| 27 | 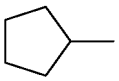 | Me | Me | H | H | H | H | H | CH₂ |
| 28 | 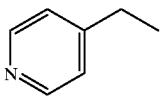 | Me | 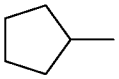 | H | H | H | H | H | — |
| 29 | 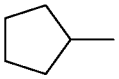 | Me | CH₃CO | H | H | H | H | H | — |
| 30 | 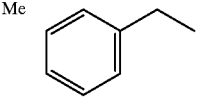 | Me | 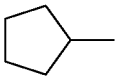 | H | H | H | H | H | — |
| 31 | 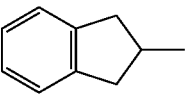 | Me | H | Et | H | H | H | H | — |
| 32 | 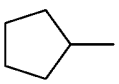 | Me | H | Et | H | H | H | H | — |
| 33 | 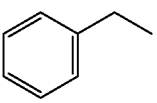 | Me | H | 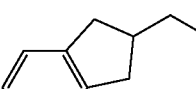 | H | H | H | H | — |
| 34 |  | Me | H | H | H | H | H | H | — |

TABLE 1-continued

| Compound No. | R₁ | R₂ | R₃ | R₄ | R₅ | R₆ | R₇ | R₈ | X |
|---|---|---|---|---|---|---|---|---|---|
| 35 | 2-(2,3-dihydro-1H-inden-2-yl)ethyl | Me | H | Me | H | H | H | H | — |
| 36 | tetrahydrofuran-3-yl | Me | H | H | H | H | H | H | — |
| 37 | tetrahydrofuran-3-yl | Me | H | Me | H | H | H | H | — |
| 38 | cyclopentyl | Me | H | H | H | H | H | H | CMe₂ |
| 39 | cyclopentyl | Me | H | H | H | H | Ph | H | CH₂ |
| 40 | cyclopentylmethyl | Me | H | H | H | H | H | H | — |
| 41 | cyclopentylmethyl | Me | H | Me | H | H | H | H | — |
| 42 | 2-(naphthalen-1-yl)ethyl | Me | H | H | H | H | H | H | — |
| 43 | 2-(naphthalen-1-yl)ethyl | Me | H | Me | H | H | H | H | — |
| 44 | norbornan-2-yl | Me | H | Me | H | H | H | H | — |

TABLE 1-continued

| Compound No. | R₁ | R₂ | R₃ | R₄ | R₅ | R₆ | R₇ | R₈ | X |
|---|---|---|---|---|---|---|---|---|---|
| 45 | norbornyl-methyl | Me | H | Et | H | H | H | H | — |
| 46 | norbornyl-methyl | Me | H | Me | H | H | H | H | CH₂ |
| 47 | norbornyl-methyl | Me | Me | Me | H | H | H | H | — |
| 48 | indanyl-methyl | Me | H | Me | H | H | H | H | CH₂ |
| 49 | 1-phenylcyclopropyl-methyl | Me | H | H | H | H | H | H | — |
| 50 | 1-phenylcyclopropyl-methyl | Me | H | Me | H | H | H | H | — |
| 51 | cyclobutyl-methyl | Me | H | H | H | H | H | H | — |
| 52 | cyclobutyl-methyl | Me | H | Me | H | H | H | H | — |
| 53 | indanyl-ethyl | Me | H | Me | H | H | H | H | CH₂ |
| 54 | cyclopentyl-ethyl | Me | H | Me | H | H | H | H | CH₂ |
| 55 | cyclohexyl-methyl | Me | H | Me | H | H | H | H | CH₂ |

TABLE 1-continued
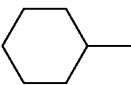
| Compound No. | R₁ | R₂ | R₃ | R₄ | R₅ | R₆ | R₇ | R₈ | X |
|---|---|---|---|---|---|---|---|---|---|
| 56 | 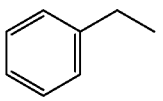 | Me | 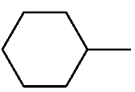 | H | H | H | H | H | — |
| 57 | 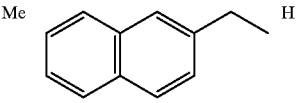 | Me | 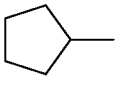 | H | H | H | H | H | — |
| 58 | 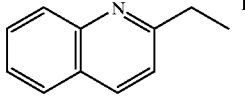 | Me | 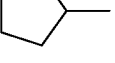 | H | H | H | H | H | — |
| 59 |  | Me | 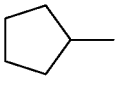 | H | H | H | H | H | — |
| 60 | 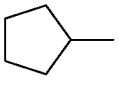 | Me | 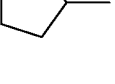 | H | H | H | H | H | — |
| 61 | 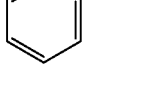 | Me | 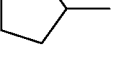 | H | H | H | H | H | — |
| 62 | 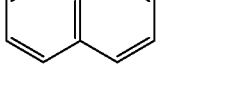 | Me | 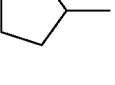 | H | H | H | H | H | — |
| 63 | 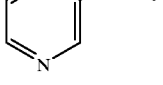 | Me | 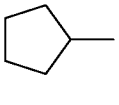 | H | H | H | H | H | — |
| 64 |  | Me | 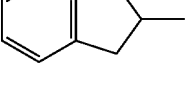 | H | H | H | H | H | — |
| 65 | 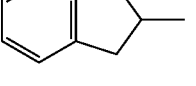 | Me | Me | H | H | H | H | H | CH₂ |
| 66 | 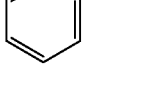 | Me | 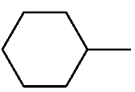 | H | H | H | H | H | CH₂ |

TABLE 1-continued

| Compound No. | R₁ | R₂ | R₃ | R₄ | R₅ | R₆ | R₇ | R₈ | X |
|---|---|---|---|---|---|---|---|---|---|
| 67 | 2-indanyl | Me | 2-naphthylmethyl | H | H | H | H | H | CH₂ |
| 68 | 2-indanyl | Me | 2-pyridylmethyl | H | H | H | H | H | CH₂ |
| 69 | cyclopentyl | Me | H | benzyl | H | H | H | H | CH₂ |
| 70 | cyclopentyl | Me | Me | Me | H | H | H | H | — |
| 71 | cyclopentyl | Me | benzyl | Me | H | H | H | H | — |
| 72 | cyclopentyl | Me | 2-quinolylmethyl | Me | H | H | H | H | — |
| 73 | 2-indanyl | Me | 4-pyridylmethyl | Me | H | H | H | H | — |
| 74 | 2-indanyl | Me | 2-naphthylmethyl | Me | H | H | H | H | — |
| 75 | cyclopentyl | Me | H | Me | H | H | H | H | CH₂ |
| 76 | 2-indanyl | Me | Me | H | H | H | H | H | — |
| 77 | 2-indanyl | Me | benzyl | H | H | H | H | H | — |

TABLE 1-continued

[Structure: R₂O and R₁O substituted phenyl connected via N(R₃) to a 6-membered ring containing X, with carbonyl (=O), and substituents R₄, R₅, R₆, R₇, R₈]

| Compound No. | $R_1$ | $R_2$ | $R_3$ | $R_4$ | $R_5$ | $R_6$ | $R_7$ | $R_8$ | X |
|---|---|---|---|---|---|---|---|---|---|
| 78 | 2-indanyl | Me | 4-pyridylmethyl | H | H | H | H | H | — |
| 79 | 2-indanyl | Me | 2-naphthylmethyl | H | H | H | H | H | — |
| 80 | 2-indanyl | Me | 2-quinolylmethyl | H | H | H | H | H | — |
| 81 | norbornyl | Me | benzyl | H | H | H | H | H | — |
| 82 | norbornyl | Me | 2-quinolylmethyl | H | H | H | H | H | — |
| 83 | norbornyl | Me | H | H | H | H | H | H | $CH_2$ |
| 84 | norbornyl | Me | benzyl | H | H | H | H | H | $CH_2$ |
| 85 | norbornyl | Me | 4-pyridylmethyl | H | H | H | H | H | $CH_2$ |

Example 86

Production of Tablets 30 g of 3-(3-cyclopentyloxy-4-methoxyanilino)-2-cyclopenten-1-one (Compound No. 1 of Table 1), 253 g of lactose, 63 g of corn starch, 40 g of low substituted hydroxypropylcellulose, and 4 g of calcium stearate were mixed and compressed by an ordinary method to prepare tablets each containing 10 mg of the compound.

Example 87

Production of Capsules 30 g of 3-[3-(1RS,2RS,4SR)-bicyclo[2.2.1]hept-2-yloxy]-4-methoxyanilino]-2-cyclopenten-1-one (Compound No. 8 of Table 1), 260 g of lactose, 66 g of corn starch, and 4 g of calcium stearate were mixed, then the mixture filled into gelatin capsules by an ordinary method to prepare capsules each containing 10 mg of the compound.

Example 88

Production of Inhalant 4-(3-cyclopentyloxy-4-methoxyanilino)-1,2,5,6-tetrahydropyridin-2-one (Compound No. 21 of Table 1) was pulverized well to reduce it to a particle size of 1 to 5 μm 0.15 g of this and 60 g of lactose (325 mesh, made by DMV Co.) were mixed. An ordinary method was used to fill this into capsules. Each capsule was adjusted to contain 50 μg of the compound. Inhalation was enabled by attaching the capsule to a powder inhalation container.

Example 89

Production of Ointment 100 mg of 4-[3-(2-indanyloxy)-4-methoxyanilino]-2-cyclopenten-1-one (Compound No. 9 of Table 1), 20 g of olive oil, and 79.9 g of white vaseline were mixed under sterile conditions.

Test Example 1

Separation of Phosphodiesterase (PDE) and Measurement of PDE Inhibitory Activity.

Type I, III, IV, and V PDE isozymes were prepared to study the PDE inhibitory activities of and selectivities with the compound of the invention [Trends Pharmacol Sci., 12, 19–27 (1991)]. Type I PDE was purchased from Sigma Corp. Type III, IV, and V PDE isozymes were partially purified from platelets (Type III and V) or neutrophils (Type IV) collected from rats. Each enzyme source was homogenized in a buffer (pH 6.5) containing 20 mM bisTris, 2 mM EDTA (i.e., ethlenediamine tetraacetate), 2-mercaptoethanol, 0.001 mM pepstatin and 0.01 mM leupeptin and was centrifuged at 30000×G for 30 minutes to obtain a supernatant, which was applied to an ion exchange column (Q-sepharose first flow, Pharmacia Corp.) and was eluted with 0 to 1M sodium acetate. Partially purified isozymes were identified by observing the inhibitory effects of conventional inhibitors.

Each PDE isozyme and the test compound dissolved in DMSO (i.e., dimethylsulfoxide) were added to 50 mM Tris—HCl buffer containing 5 mM magnesium chloride. $^3$H-cAMP (for type III and IV PDE) or $^3$H-cGMP (for type I and V PDE) were added as substrates and were reacted at 30° C. for 30 minutes. The reaction was terminated by placing the test tube in boiling water of 100° C. for 5 minutes. The nucleotides formed by PDE were broken down to $^3$H-adenosine or $^3$H-guanosine by 5'-nucleotidase. The substrate and reaction product were separated through an ion-exchange column (i.e., QAE sephadex, Pharmacia Corp.)

The eluted $^3$-H-nucleoside was measured for its radioactivity by a liquid scintillation counter. The inhibitory activities of the compound of the present invention are shown by the IC$_{50}$ value (M). The inhibition of type IV PDE is shown in Table 2. Further, the inhibitory activities of the test samples against type I, III, and V PDE are 1/10 or less than that against Type IV PDE.

TABLE 2

| Compound No. | PDE IV inhibiting action IC$_{50}$ (M) |
|---|---|
| 1 | $1.6 \times 10^{-6}$ |
| 2 | $3.7 \times 10^{-6}$ |
| 3 | $4.9 \times 10^{-6}$ |
| 4 | $3.9 \times 10^{-7}$ |
| 5 | $2.2 \times 10^{-6}$ |
| 6 | $5.4 \times 10^{-7}$ |
| 7 | $2.8 \times 10^{-7}$ |
| 8 | $1.3 \times 10^{-6}$ |
| 9 | $6.9 \times 10^{-7}$ |
| 10 | $1.4 \times 10^{-7}$ |
| 11 | $4.0 \times 10^{-6}$ |
| 12 | $7.1 \times 10^{-7}$ |
| 13 | $7.4 \times 10^{-6}$ |
| 14 | $2.4 \times 10^{-6}$ |
| 15 | $7.1 \times 10^{-6}$ |
| 16 | $1.0 \times 10^{-6}$ |
| 17 | $1.4 \times 10^{-5}$ |
| 18 | $1.7 \times 10^{-6}$ |
| 19 | $1.8 \times 10^{-6}$ |
| 20 | $4.4 \times 10^{-5}$ |
| 21 | $1.1 \times 10^{-6}$ |
| 22 | $2.4 \times 10^{-5}$ |
| 23 | $2.4 \times 10^{-6}$ |
| 24 | $6.1 \times 10^{-5}$ |
| 25 | $1.7 \times 10^{-5}$ |
| 26 | $8.0 \times 10^{-7}$ |
| 27 | $1.9 \times 10^{-6}$ |
| 28 | $4.3 \times 10^{-6}$ |
| 29 | $4.8 \times 10^{-5}$ |
| 30 | $2.6 \times 10^{-6}$ |
| 31 | $2.2 \times 10^{-7}$ |
| 32 | $5.0 \times 10^{-8}$ |
| 33 | $4.0 \times 10^{-7}$ |
| 34 | $1.8 \times 10^{-6}$ |
| 35 | $2.9 \times 10^{-7}$ |
| 36 | $8.9 \times 10^{-6}$ |
| 37 | $1.2 \times 10^{-6}$ |
| 38 | $1.7 \times 10^{-5}$ |
| 39 | $3.9 \times 10^{-6}$ |
| 40 | $4.0 \times 10^{-6}$ |
| 41 | $9.4 \times 10^{-7}$ |
| 42 | $9.6 \times 10^{-6}$ |
| 43 | $1.3 \times 10^{-6}$ |
| 44 | $2.2 \times 10^{-7}$ |
| 45 | $8.0 \times 10^{-8}$ |
| 46 | $2.6 \times 10^{-7}$ |
| 47 | $1.6 \times 10^{-6}$ |
| 48 | $8.2 \times 10^{-8}$ |
| 49 | $2.3 \times 10^{-6}$ |
| 50 | $6.2 \times 10^{-7}$ |
| 51 | $1.9 \times 10^{-6}$ |
| 52 | $5.5 \times 10^{-7}$ |
| 53 | $2.2 \times 10^{-7}$ |
| 54 | $7.3 \times 10^{-7}$ |
| 55 | $2.0 \times 10^{-6}$ |
| 56 | $5.5 \times 10^{-6}$ |
| 57 | $1.9 \times 10^{-6}$ |
| 58 | $5.3 \times 10^{-7}$ |
| 59 | $7.4 \times 10^{-6}$ |
| 60 | $4.4 \times 10^{-5}$ |
| 61 | $3.2 \times 10^{-6}$ |
| 62 | $1.2 \times 10^{-6}$ |
| 63 | $5.3 \times 10^{-6}$ |
| 64 | $4.4 \times 10^{-6}$ |
| 65 | $2.9 \times 10^{-7}$ |
| 66 | $5.7 \times 10^{-7}$ |
| 67 | $3.8 \times 10^{-6}$ |
| 68 | $4.9 \times 10^{-7}$ |
| 69 | $1.1 \times 10^{-6}$ |
| 70 | $3.1 \times 10^{-6}$ |
| 71 | $8.2 \times 10^{-6}$ |
| 72 | $3.0 \times 10^{-6}$ |
| 73 | $3.2 \times 10^{-6}$ |
| 74 | $3.5 \times 10^{-6}$ |
| 75 | $4.7 \times 10^{-7}$ |
| 76 | $1.3 \times 10^{-7}$ |
| 77 | $9.1 \times 10^{-7}$ |
| 78 | $1.3 \times 10^{-6}$ |
| 79 | $7.3 \times 10^{-7}$ |
| 80 | $1.2 \times 10^{-7}$ |
| 81 | $1.0 \times 10^{-6}$ |
| 82 | $5.3 \times 10^{-7}$ |
| 83 | $1.6 \times 10^{-6}$ |
| 84 | $1.4 \times 10^{-6}$ |
| 85 | $3.6 \times 10^{-6}$ |

Test Example 2

Inhibitory Effects on Activity of Rat Neutrophils

The release of super oxide anions was measured so as to study the inhibitory effects of the compound of the present invention on inflammatory leukocytes, that is, neutrophils.

Blood sample was collected from Wister rats anestetized with ether. It was superposed on a blood cell separation solution (Polymorphoprep 1.113, Naicomed Farm) and the neutrophils were separated by centrifugation. The neutrophils were resuspended in a Hank's balanced salt solution at a concentration of $0.5 \times 10^4$ cells/ml. 0.1 mM of lusigenin and the test substance dissolved in DMSO were added to 2 ml of the cell suspension. The chemiluminescence generated by stimulation of 0.3 maicro M calcium ionophore A23187 was measured by a chemiluminescence reader so as to evaluate the release of super oxide anions. The efficacy of the compounds of the present invention was expressed by an $IC_{50}$ value and is shown in Table 3.

TABLE 3

| Compound No. | Action suppressing release of superoxide anions from rat neutrophils $IC_{50}$ (M) |
|---|---|
| 1 | $1.2 \times 10^{-7}$ |
| 8 | $1.4 \times 10^{-7}$ |
| 21 | $4.1 \times 10^{-7}$ |
| 22 | $3.3 \times 10^{-6}$ |
| 23 | $1.9 \times 10^{-7}$ |

Test Example 3

Inhibitory Effect on Antigen-Induced Bronchospasm (Anti-Asthmatic Action)

Hartley male guinea-pig was sensitized by intramuscular administration of 35 mg Ovalbumin (OA) at first day and fourth day. After 25 to 29 days of first sensitization, trachial canula was introduced in the guinea pig anesthetized with pentobarbital and artificial ventilation was performed. The overflow of the ventilation was measured by the Konzett Roessler method while 0.2 mg/kg OA were administered intravenously. The test compound was dissolved in polyethylene glycol 400 and intravenously administered 10 minutes before OA challenge. The effect of the present invention was expressed by the $ED_{50}$ value and is shown in Table 4.

TABLE 4

| Compound No. | Action suppressing antigen induced bronchoconstriction $ED_{50}$ (mg/kg) |
|---|---|
| 1 | 1.4 |
| 8 | 3.0 |
| 9 | 5.5 |
| 10 | 0.86 |
| 21 | 1.0 |
| 32 | 7.34 |

Test Example 4

TPA Induced Mouse Ear Edema Assay

Male ICR mice, 5 week old, were divided into groups of seven to eight. 2 μg of TPA (phorbor 12-ministate; Sigma Co.) in 20 μl acetone was applied to the inner and outer surface of right ear of each mouse to cause a reaction. 0.1 mg of compound was dissolved in 20 μl of a tetrahydrofuran-methanol mixture (mixture ratio 1:1) and the solution (20 μl) applied to the right ear immediately after TPA treatment. After 6 hour, the animals were sacrificed and right ear was punched out (φ 6 nm) and weighed. The effect of comppund.was calculated as % inhibition as follows:

% inhibition=

$$100 - \left\{ \frac{TPA \text{ and compound treated} - \text{baseline control}}{\text{stimulated control}/(TPA) - \text{baseline control}} \times 100 \right\}$$

The value was shown in Table 5.

TABLE 5

| Compound No | % Inhibition of ear edema |
|---|---|
| 1 | 68.2 |
| 2 | 65.0 |
| 7 | 55.8 |
| 8 | 73.1 |
| 9 | 72.3 |
| 12 | 52.5 |
| 13 | 51.8 |
| 14 | 73.4 |
| 16 | 72.1 |
| 17 | 57.1 |
| 19 | 76.3 |
| 22 | 76.8 |
| 23 | 73.0 |
| 26 | 82.0 |
| 27 | 86.4 |
| 28 | 71.5 |
| 30 | 78.4 |
| 31 | 73.4 |
| 32 | 75.5 |
| 33 | 81.7 |
| 35 | 52.5 |
| 37 | 51.8 |
| 44 | 74.1 |
| 45 | 75.3 |
| 47 | 59.9 |
| 48 | 53.8 |
| 49 | 54.3 |
| 50 | 62.6 |
| 53 | 55.9 |
| 55 | 70.8 |
| 56 | 86.1 |
| 57 | 89.7 |
| 58 | 58.7 |
| 59 | 60.1 |
| 60 | 78.5 |
| 61 | 66.2 |
| 62 | 78.8 |
| 63 | 75.4 |
| 64 | 52.0 |
| 65 | 52.5 |
| 66 | 72.8 |
| 67 | 60.8 |
| 68 | 52.0 |
| 73 | 54.3 |
| 75 | 64.8 |
| 76 | 52.7 |
| 77 | 50.9 |
| 78 | 82.2 |
| 79 | 89.0 |
| 80 | 64.4 |
| 81 | 82.7 |
| 82 | 84.4 |
| 83 | 70.5 |
| 84 | 71.8 |
| 85 | 70.3 |

Test Sample 5

Allergic Contact Dermatitis Assay 8 to 9 week old ICR type male mice were divided into groups of 8 to 9 each for use. The shaved skin of the ventral surface of each of the mice was applied with a 0.5% DNFB (2,4-dinitrofluorobenzene)acetone-olive oil solution (v/v=4/1) in an amount of 25 μl/day over 2 days to sensitize it. Four days after the second day of sensitization, a 0.2% DNFB acetone-olive oil solution was applied to the ear in an amount of 25 μl to induce contact-type dermatitis. After 24 hours, the thickness of the ear was measured using a dial thickness gauge and the difference with the value before inducing the edema was found. The test compound was dissolved in 25 μl of tetrahydrofuran-methanol (mixture ratio 1:1) and applied two time, that is, 1 hour before inducing the ear edema and 5 hours after it.

In Table 6, the effect of the compound was expressed by the $ED_{50}$.

TABLE 6

| Compound No. | $ED_{50}$ (μg/site) |
|---|---|
| 9 | 94 |
| 14 | 16 |
| 22 | 32 |

Test Example 6

Acute Toxicity Test

Compounds of the present invention of Nos 1 to 85 in Table 1 were suspended in a saline containing 0.5% sodium carboxylmethylcellulose and were administered ddy male mouse intraperitoneally. The survival rate of the next day was examined. No death was observed at a dosage of 30 mg/kg of any compound.

Industrial Applicability

The compound of the present invention has a superior PDE IV inhibiting action and is useful as a drug for the treatment of asthma, dermatitis, and other inflammatory diseases; multiple sclerosis; and rheumatism and other autoimmune diseases.

What is claimed is:

1. A 3-anilino-2-cycloalkenone derivative having the formula (I):

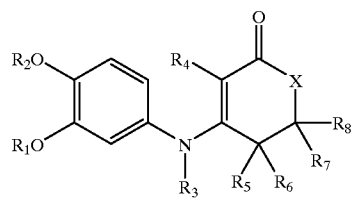

(I)

wherein $R_1$ represents a $C_3$ to $C_8$ alkyl group which may have a substituent, a $C_3$ to $C_7$ cycloalkyl group, a $C_6$ to $C_{10}$ bicycloalkyl group, a 3-tebrahydrofuryl group, or an indanyl group, $R_2$ represents a $C_1$ to $C_4$ alkyl group, $R_3$ respresents a hydrogen atom, a $C_1$ to $C_5$ alkyl group, which may have a substituent, a $C_3$ to $C_7$ cycloalkyl group, or an acyl group, $R_4$ represents a hydrogen atom, a $C_1$ to $C_5$ alkyl group which may have a substituent, a halogen atom, a group having the formula (II):

(II)

wherein $R_9$ and $R_{10}$ independently represent a $C_1$ to $C_5$ alkyl group, or a group having the formula (III):

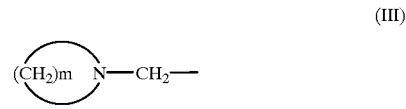

(III)

wherein, m represents an integer of 2 to 6, provided that one $CH_2$ group may be substituted with one hetero atom selected from the group consisting of oxygen, nitrogen, and sulfur, $R_5$, $R_6$, $R_7$, and $R_8$ independently represent a hydrogen atom, a $C_1$ to $C_5$ alkyl group which may have a substituent, or a phenyl group which may have a substituent, X represents (i) —$(CR_{11}R_{12})n$— wherein $R_{11}$, and $R_{12}$ independently represent a hydrogen atom, a $C_1$ to $C_5$ alkyl group which may have a substituent, or a phenyl group which may have a substituent, and n represents an integer of 0 or 2 or (ii) —$NR_{13}$— wherein $R_{13}$ represents a hydrogen atom or a $C_1$ to $C_5$ alkyl group which may have a substituent, provided that, when n is 0, X in the formula (I) is absent and the carbon atoms bonded to X in the formula (I) are bonded together to form a 5-membered ring, and its optical isomers or their pharmaceutically acceptable salts or their hydrates or solvates.

2. A compound as claimed in claim 1, wherein $R_1$ is a $C_4$ to $C_6$ alkyl group, a $C_4$ to $C_7$ cycloalkyl group, a $C_6$ to $C_8$ bicycloalkyl group, a $C_1$ to $C_5$ alkyl group having as a substituent, a phenyl group, a naphthyl group, an indanyl group, or a $C_3$ to $C_7$ cycloalkyl group which may have a substituent, a 3-tetrahydrofuryl group, or an indanyl group.

3. A compound as claimed in claim 2, wherein $R_1$ is a butyl group, a cyclopropyl group, a cyclopentyl group, a cyclohexyl group, a cyclopropylmethyl group, a cyclobutylmethyl group, a cyclopentylmethyl group, a (1-phenylcyclopropyl)methyl group, a benzyl group, a phenethyl group, a 2-(1-naphthyl)ethyl group, a 2-(2-indanyl)ethyl group, a (1RS, 2RS, 4SR) bicyclohept-2-yl group, a 3-tetrahydrofuryl group, or an 2-indanyl group.

4. A compound as claimed in claim 1, wherein $R_2$ is a methyl group.

5. A compound as claimed in claim 1, wherein $R_3$ is a hydrogen atom, a methyl group, an ethyl group, a propyl group, a butyl group, a pentyl group, a 2-pyridylmethyl group, a 3-pyridylmethyl group, a 4-pyridylmethyl group, a benzyl group, a 1-naphthylmethyl group, a 2-naphthylmethyl group, a 2-quinolylmethyl group, a cyclopentyl group, or an acetyl group.

6. A compound as claimed in claim 1, wherein $R_4$ is a hydrogen atom, a halogen atom, a methyl group, an ethyl group, a dimethylaminomethyl group, a morpholinomethyl group, or a benzyl group.

7. A compound as claimed in claim 1, wherein, in X, n in the —$(CR_{11}R_{12})_n$— is 0, provided that, when n is 0, X in the formula (I) is absent and the carbon atoms bonded to X in the formula (I) are bonded together to form a 5-membered ring, and $R_{11}$ and $R_{12}$ are independently a hydrogen atom or a methyl group or the $R_{13}$ of the —$NR_{13}$— is a hydrogen atom, a $C_1$ to $C_3$ alyl group, or a benzyl group.

8. A compound as claimed in claim 1, wherein $R_5$, $R_6$, $R_7$, and $R_8$ are, independently, a hydrogen atom or a methyl group.

9. A pharmaceutical composition containing a compound as claimed in claim 1.

10. A method for treating an inflammatory disease comprising administering a drug comprising a compound according to claim 1 and a pharmacologically acceptable carrier.

11. A method for treating asthma comprising administering a drug comprising a compound according to claim 1 and a pharmacologically acceptable carrier.

12. A method for treating dermatitis comprising administering a drug comprising a compound according to claim 1 and a pharmacologically acceptable carrier.

* * * * *

UNITED STATES PATENT AND TRADEMARK OFFICE
CERTIFICATE OF CORRECTION

PATENT NO.   : 6,235,736 B1
DATED        : May 22, 2001
INVENTOR(S)  : Shinji Ina, Kenjirou Yamana, Kyoji Noda, Akane Takahama and Toshihiko Akiyama It is certified that error appears in the above-identified patent and that said Letters Patent is hereby corrected as shown below:

<u>Title page,</u>
Item [56], References Cited, OTHER PUBLICATIONS, in "N. Sommer et al." replace "Autoimmune Encephalomyelits" with -- Autoimmune Encephalomyelitis --.
Item [57], ABSTRACT,
Line 5, after Forumula I, replace "$C_3$ to $C_7$" with -- $C_1$ to $C_5$ --.

<u>Column 55,</u>
Line 61, replace "$C_3$ to $C_8$" with -- $C_1$ to $C_8$ --.
Line 63, replace "3-tebrahydrofuryl" with -- 3-tetrahydrofuryl --.

<u>Column 56,</u>
Line 48, replace "bicyclohept-2-yl" with -- bicyclo[2.2.1]hept-2-yl --.

<u>Column 57,</u>
Line 2, replace "alyl" with -- alkyl --.

Signed and Sealed this

Twenty-second Day of October, 2002

Attest:

JAMES E. ROGAN
Attesting Officer          Director of the United States Patent and Trademark Office